(12) United States Patent
Cavalcanti et al.

(10) Patent No.: US 7,304,014 B2
(45) Date of Patent: Dec. 4, 2007

(54) MODIFIED CATALYSTS AND PROCESS

(75) Inventors: Fernando Antonio Pessoa Cavalcanti, Lafayette Hill, PA (US); Sanjay Chaturvedi, Lansdale, PA (US); Anne Mae Gaffney, West Chester, PA (US); Scott Han, Lawrenceville, NJ (US); Ruozhi Song, Wilmington, DE (US); Elsie Mae Vickery, Jenkintown, PA (US)

(73) Assignee: Rohm and Haas Company, Philadelphia, PA (US)

( * ) Notice: Subject to any disclaimer, the term of this patent is extended or adjusted under 35 U.S.C. 154(b) by 125 days.

(21) Appl. No.: 11/071,137

(22) Filed: Mar. 3, 2005

(65) Prior Publication Data

US 2005/0202965 A1 Sep. 15, 2005

Related U.S. Application Data

(60) Provisional application No. 60/551,820, filed on Mar. 10, 2004.

(51) Int. Cl.
*B01J 23/00* (2006.01)
*B01J 23/02* (2006.01)
*B01J 23/06* (2006.01)

(52) U.S. Cl. .............. 502/300; 502/305; 502/308; 502/313; 502/317; 502/319; 502/325; 502/340; 502/344; 502/349; 502/353; 502/355

(58) Field of Classification Search ......... 502/305–355
See application file for complete search history.

(56) References Cited

U.S. PATENT DOCUMENTS

| | | | |
|---|---|---|---|
| 4,419,270 A | 12/1983 | Ueshima et al. | |
| 4,824,869 A * | 4/1989 | Prada-Silva et al. | |
| 5,380,933 A | 1/1995 | Ushikubo | |
| 5,908,658 A * | 6/1999 | Dougherty et al. | |
| 6,043,185 A | 3/2000 | Cirjak et al. | |
| 6,080,882 A * | 6/2000 | Midorikawa et al. | ....... 558/319 |
| 6,383,978 B1 | 5/2002 | Bogan, Jr. | |
| 6,403,525 B1 | 6/2002 | Chaturvedi et al. | |

(Continued)

FOREIGN PATENT DOCUMENTS

EP 0608838 8/1994

(Continued)

OTHER PUBLICATIONS

Ueda W. et al: "Selective oxidation of light alkanes over hydrothermally synthesized Mo-V-M-O (M=Al, Ga, Bl, Sb, and Te) oxide catalysts" Aug. 28, 2000, Applied Catalysis A: General, Elsevier Science, Amsterdam, NL, pp. 135-143, XP004272455.

*Primary Examiner*—J. A. Lorengo
*Assistant Examiner*—Patricia L. Hailey
(74) *Attorney, Agent, or Firm*—Marcella M. Bodner

(57) ABSTRACT

Modified metal oxide catalysts are disclosed which have different chemical, physical and catalytic properties, when used for catalytic conversions of carbon based compounds, as compared to corresponding unmodified metal oxide catalysts. Methods for preparing the modified catalysts are described and their utility in catalytic process is described. Alkenes, unsaturated saturated carboxylic acids, saturated carboxylic acids and their higher analogues are prepared directly from corresponding alkanes, alkenes or alkanes and alkenes utilizing using one or more modified metal oxide catalysts.

3 Claims, 2 Drawing Sheets

U.S. PATENT DOCUMENTS

Figure 1:
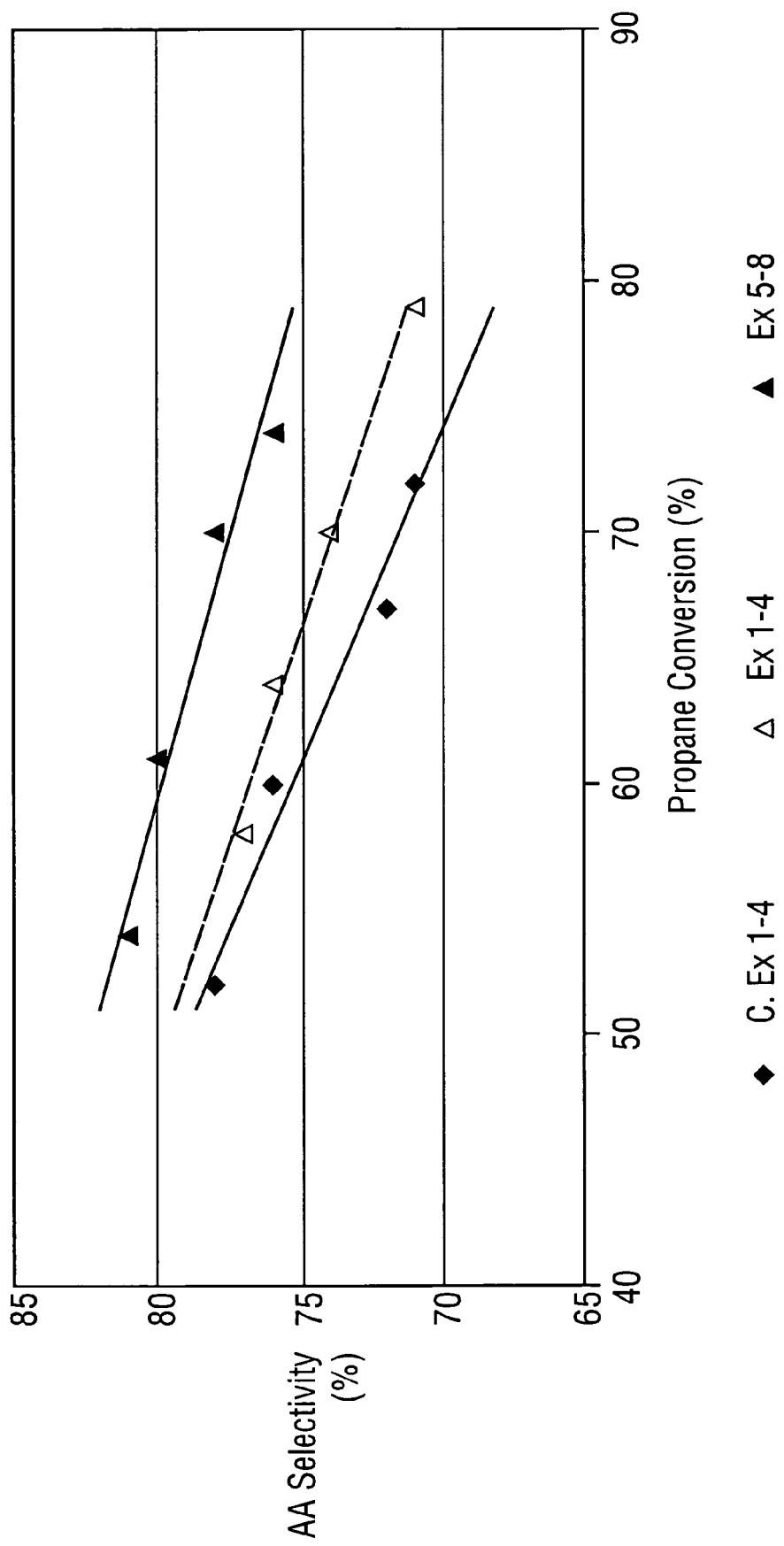

| | | | |
|---|---|---|---|
| 6,407,031 B1 | 6/2002 | Chaturvedi et al. | |
| 6,407,280 B1 | 6/2002 | Chaturvedi et al. | |
| 6,472,552 B1 * | 10/2002 | Bogan, Jr. | 558/319 |
| 6,504,053 B1 | 1/2003 | Chaturvedi et al. | |
| 6,518,216 B1 | 2/2003 | Han et al. | |
| 6,589,907 B2 | 7/2003 | Chaturvedi et al. | |
| 6,613,708 B1 * | 9/2003 | Ou et al. | |
| 6,624,111 B2 | 9/2003 | Chaturvedi et al. | |
| 6,641,996 B1 | 11/2003 | Jefferson et al. | |
| 6,656,873 B2 * | 12/2003 | Chaturvedi et al. | 502/312 |
| 6,777,571 B2 * | 8/2004 | Chaturvedi et al. | 558/323 |
| 6,818,588 B2 * | 11/2004 | Gaffney et al. | 502/311 |
| 6,914,150 B2 * | 7/2005 | Gaffney et al. | 558/319 |
| 6,919,295 B2 * | 7/2005 | Gaffney et al. | |
| 6,943,135 B2 * | 9/2005 | Gaffney et al. | |
| 6,982,343 B2 * | 1/2006 | Chaturvedi et al. | |
| 7,018,951 B2 * | 3/2006 | Gaffney et al. | |
| 2002/0183547 A1 | 12/2002 | Gaffney et al. | |
| 2003/0004379 A1 | 1/2003 | Gaffney et al. | |
| 2003/0144539 A1 | 7/2003 | Mamedov et al. | |
| 2004/0132832 A1 * | 7/2004 | Espinoza et al. | |
| 2005/0203312 A1 * | 9/2005 | Cavalcanti et al. | |
| 2005/0239643 A1 * | 10/2005 | Benderly et al. | |
| 2006/0122055 A1 * | 6/2006 | Gaffney et al. | |
| 2006/0183942 A1 * | 8/2006 | Gaffney et al. | |

FOREIGN PATENT DOCUMENTS

| | | |
|---|---|---|
| EP | 0630879 | 12/1994 |
| EP | 1192894 | 4/2002 |
| EP | 1192982 | 4/2002 |
| EP | 1192983 | 4/2002 |
| EP | 1192986 | 4/2002 |
| EP | 1192987 | 4/2002 |
| EP | 1192988 | 4/2002 |
| EP | 1193240 | 4/2002 |
| EP | 1249274 | 10/2002 |
| EP | 1254707 | 11/2002 |
| EP | 1407819 | 4/2004 |
| EP | 1080784 | 4/2005 |
| EP | 1531001 | 5/2005 |
| JP | 08057319 | 3/1996 |
| JP | 2000/037623 | 2/2000 |
| WO | WO00/29106 | 5/2000 |
| WO | WO03/039745 | 5/2003 |

* cited by examiner

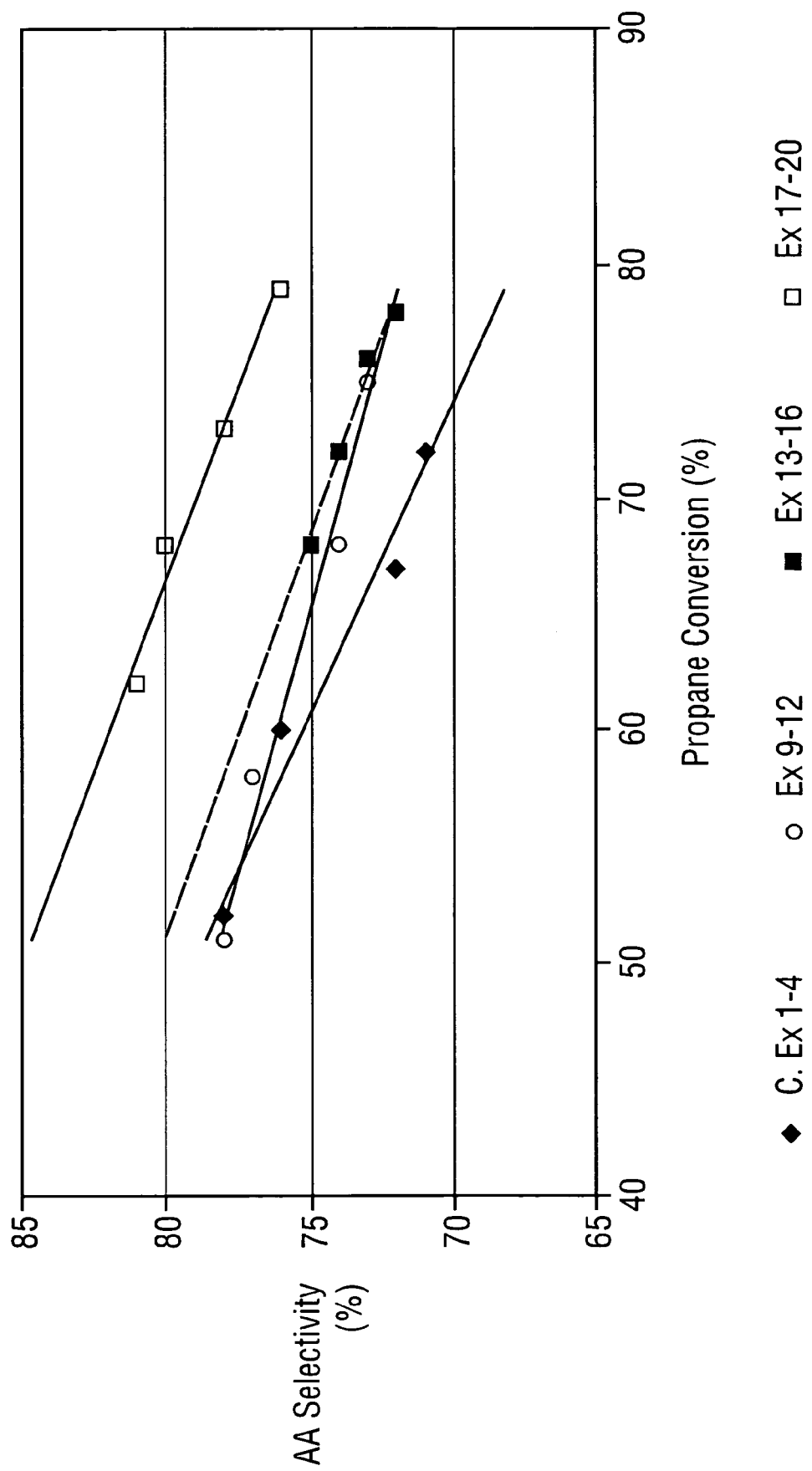

MODIFIED CATALYSTS AND PROCESS

CROSS REFERENCE TO RELATE PATENT APPLICATIONS

This is a non-provisional patent application of U.S. provisional patent application Ser. No. 60/551,820 filed Mar. 10, 2004.

The present invention relates to modifying and thereby improving metal oxide catalysts, as compared to corresponding unmodified metal oxide catalysts, used for catalytically converting alkanes, alkenes and mixtures thereof to their corresponding oxygenates, including unsaturated carboxylic acids and esters thereof, by vapor phase oxidation. In particular, the invention is directed to chemical and/or physical modifications of prepared metal oxide catalysts, which in turns improves their efficiency and selectivity for converting alkanes, alkenes and mixtures thereof to their corresponding oxygenates. The invention is further directed to treated mixed metal oxide catalysts; methods for preparing treated mixed metal oxide catalysts and to processes using the treated metal oxide catalysts in vapor phase catalytic processes, including catalytic oxidations of alkanes, alkenes and mixtures thereof.

The selective partial oxidation of alkenes to unsaturated carboxylic acids and their corresponding esters is an important commercial process. However, the selective and efficient partial oxidation/dehydrogenation of alkanes to products including olefins, unsaturated carboxylic acids and esters of unsaturated carboxylic acids is not optimized in large part due to an optimal catalyst and has remained a catalytic process with a number of challenges to overcome.

U.S. Pat. No. 6,043,185 discloses a catalyst useful in the manufacture of acrylonitrile or methacrylonitrile by catalytic reaction in the vapor phase of a paraffin selected from propane and isobutane with molecular oxygen and ammonia by catalytic contact of the reactants in a reaction zone with a catalyst, wherein the catalyst has the empirical formula $$Mo_aV_bSb_cGa_dX_eO_x$$

where X is one or more of As, Te, Se, Nb, Ta, W, Ti, Zr, Cr, Mn, Fe, Ru, Co, Rh, Ni, Pd, Pt, B, In, Ce, Re, Ir, Ge, Sn, Bi, Y, Pr, an alkali metal and an alkaline earth metal; and when a=1, b=0.0 to 0.99, c=0.01 to 0.9, d=0.01 to 0.5, e=0.0 to 1.0 and x is determined by the oxidation state of the cations present. Ammonia is used as a reactant with co-reactant alkanes and molecular oxygen, however, and there is no disclosure of treating the oxidation catalyst with ammonia after the catalysts has been prepared or before the catalytic process is initiated. Despite the above-noted and other attempts to provide new and improved catalysts for the oxidation of alkanes to unsaturated carboxylic acids, no attempts have been made to modify existing catalysts used for the process. Moreover, one impediment to the provision of a commercially viable process for such catalytic oxidations is the identification of an optimal catalyst, catalysts or catalyst system that provides adequate conversion and suitable selectivity, which in turn provides sufficient yield of the corresponding unsaturated product.

The inventors have discovered that modifying prepared mixed metal oxide catalysts useful for converting alkanes, alkenes and mixtures thereof to their corresponding oxygenates by subjecting the prepared catalysts to chemical, physical and combinations of chemical and physical treatments (referred to as "post treatment" of prepared catalysts) results in unexpected improvements in catalyst efficiency and selectivity in such conversions and unexpected changes in catalyst properties, including catalyst structure, density and surface area as compared to unmodified catalysts. Inventors have further discovered, for example, that modified (post treated) mixed metal oxide catalysts unexpectedly provide improved selectivities and yields of oxygenates including unsaturated carboxylic acids from their corresponding alkanes at constant alkane conversion as compared to corresponding unmodified (untreated) mixed metal oxide catalysts.

Accordingly, there is provided a modified catalyst comprising: one or more metal oxide catalysts altered using one or more chemical treatments, one or more physical treatments or the combination of one or more chemical and physical treatments, wherein the modified catalyst exhibits one or more differences in chemical, physical and structural properties, including improved catalyst performance and catalyst properties as compared to the unmodified catalyst. According to one embodiment, the modified catalyst comprises one or more modified mixed metal oxide catalysts having the empirical formula:

$$M_eMoV_aNb_bX_cZ_dO_n$$

wherein $M_e$ is at least one or more chemical modifying agents, X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, Y, rare earth elements and alkaline earth elements, $0.1 \leq a \leq 1.0$, $0.01 \leq b \leq 1.0$, $0.01 \leq c \leq 1.0$, $0 \leq d \leq 1.0$ and n, e are determined by the oxidation states of the other elements. According to a separate embodiment, the modified catalyst comprises one or more modified mixed metal oxide catalysts having the empirical formula:

$$MoV_aNb_bX_cZ_dO_n$$

wherein X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, Y, rare earth elements and alkaline earth elements, $0.1 \leq a \leq 1.0$, $0.01 \leq b \leq 1.0$, $0.01 \leq c \leq 1.0$, $0 \leq d \leq 1.0$; n is determined by the oxidation states of the other elements and wherein the modified catalyst has improved catalytic performance characteristics and catalyst properties as compared to an unmodified catalyst comprising the corresponding one or more modified mixed metal oxide catalysts having the empirical formula described above. Chemical treatments include one or more chemical modifying agents, physical treatments include, but are not limited to, cooling, cryogenic cooling, pressure cooling, compacting under pressure, high pressure die pressing, thermolyzing (also referred to as polymer burn off), mechanical grinding at cryogenic temperatures, high shear grinding at cryogenic temperatures, cryo-milling, cryo-densifying, cryo-stressing, cryo-fracturing, cryo-pelletizing, deforming, wash coating, molding, forming, shaping, casting, machining, laminating, drawing, extruding, lobalizing, impregnating, forming spheres (spherolizing), slurrying, cryo-slurrying, preparing shelled catalysts (shelling), multi-coating, electrolyzing, electrodepositing, compositing, foaming, cryo-fluidizing, cryo-spraying, thermal spraying, plasma spraying, vapor depositing, adsorbing, ablating, vitrifying, sintering, cryo-sintering, fusing, fuming, crystallizing, any altering of catalyst crystal structure, polycrystallizing, recrystallizing, any surface treating of the catalyst, any altering of catalyst surface structure, any altering of catalysts porosity, any altering of catalyst surface area, any altering of catalyst density, any altering of bulk catalysts structure, reducing the particle size of the primary catalyst particles in combination with cooling or thermolyzing the catalyst, and any combinations of chemical and physical treatments, including but not limited to solvent extraction, Soxhlet extraction, batch solvent extraction, continuous flow solvent extraction, extraction in supercritical solvents, contacting the catalyst with one or more leaching agents including solvents, altering catalyst pH, any chemical treatments used in modifying catalyst surface structure, mechanical grinding in supercritical solvents, chemisorbing one or more chemical agents, ultrasonification using one or more solvents selected from organic solvents such as alcohols and amines ultrasonification, and any physical treatments employing solvents under supercritical conditions. According to a separate embodiment, modified catalysts include one or more further chemical and/or physical treatments of already modified catalysts.

The present invention also provides a process for improving one or more performance characteristics of a metal oxide catalyst, comprising the steps of:
 a) preparing or obtaining one or more metal oxide catalysts;
 b) treating the one or more metal oxide catalysts with one or more chemical treatments, one or more physical treatments and one or more combinations of chemical and physical treatments; and optionally,
 c) further modifying the one or more modified metal oxide catalysts using one or more chemical treatments, one or more physical treatments and one or more combinations of chemical and physical treatments;

wherein catalyst performance characteristics of the one or more modified metal oxide catalysts are improved as compared to corresponding performance characteristics of the one or more unmodified metal oxide catalysts. According to one embodiment, the modified catalyst is a modified mixed metal oxide catalyst and the modified mixed metal oxide catalyst unexpectedly provides improved selectivities and yields of oxygenates including unsaturated carboxylic acids from their corresponding alkanes at constant alkane conversion as compared to corresponding unmodified mixed metal oxide catalysts.

The invention also provides a process for preparing one or more modified metal oxide catalysts, comprising the steps of:
 a) providing one or more prepared metal oxide catalysts;
 b) treating the one or more prepared metal oxide catalysts with one or more chemical treatments, one or more physical treatments and one or more combinations of chemical and physical treatments; and optionally,
 c) further modifying the one or more modified metal oxide catalysts using one or more chemical treatments, one or more physical treatments and one or more combinations of chemical and physical treatments;

wherein catalyst properties of the one or more modified metal oxide catalyst are improved as compared to corresponding catalyst properties of the one or more unmodified metal oxide catalysts. According to one embodiment, the modified catalyst is a modified mixed metal oxide catalyst and the modified mixed metal oxide catalyst unexpectedly provides improved selectivities and yields of oxygenates including unsaturated carboxylic acids from their corresponding alkanes at constant alkane conversion as compared to corresponding unmodified mixed metal oxide catalysts.

The present invention also provides a process for producing an unsaturated carboxylic acid, which comprises subjecting an alkane, alkene or a mixture of an alkane and an alkene to a vapor phase catalytic oxidation reaction in the presence of one or more modified metal oxide catalysts comprising the step of contacting the alkane, alkene or a mixture of an alkane and an alkene with (a) one or more metal oxide catalysts (b) one or more chemical treatments, one or more physical treatments and one or more combinations of chemical and physical treatments, wherein yield and selectivity of the unsaturated carboxylic acid is improved using the one or more modified metal oxide catalysts as compared to the one or more corresponding unmodified metal oxide catalysts. According to one embodiment, one class of modified catalyst compositions is obtained by treating one or more prepared mixed metal oxide catalysts having the empirical formula:

$$MoV_aNb_bX_cZ_dO_n$$

wherein X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, Y, rare earth elements and alkaline earth elements, $0.1 \leq a \leq 1.0$, $0.01 \leq b \leq 1.0$, $0.01 \leq c \leq 1.0$, $0 \leq d \leq 1.0$ and n is determined by the oxidation states of the other elements.

The invention also provides a process for preparing unsaturated carboxylic acids from corresponding alkanes, alkenes, or corresponding alkanes and alkenes, the process comprising the step of:
 passing a gaseous alkane, alkene or alkane and alkene, and molecular oxygen to a reactor, the reactor including one or more modified metal oxide catalysts, the one or more modified metal oxide catalysts cumulatively effective at converting the gaseous alkane, alkene, or alkane and alkene to its corresponding gaseous unsaturated carboxylic acid;
 wherein the reactor is operated at a temperature of from 100° C. to 600° C. According to one embodiment, one or more modified mixed metal oxide catalysts are used and a conventional reactor is used with the alkane or alkane and alkene having a reactor residence time of greater than 100 milliseconds. According to a separate embodiment, a short contact time reactor is used with the alkane or alkane and alkene having a reactor residence time of no greater than 100 milliseconds.

As used herein, the term "modified catalyst" which is equivalent to "treated catalysts" which is also equivalent to "post-treated catalysts" refers to any chemical, physical and combinations of chemical and physical modification or modifications of one or more prepared catalysts as compared to corresponding catalysts having undergone no such modification or modifications (also referred to as unmodified catalysts, equivalently referred to as untreated catalysts). Modifications to prepared catalysts include, but are not limited to, any differences in the modified catalysts as compared to corresponding unmodified catalysts. Suitable modifications to catalysts include, for example, structural changes, spectral changes (including position and intensity of characteristic X-ray diffraction lines, peaks and patterns), spectroscopic changes, chemical changes, physical changes, compositional changes, changes in physical properties, changes in catalytic properties, changes in performance characteristics in conversions of organic molecules, changes in yields of organic products from corresponding reactants, changes in catalyst activity, changes in catalyst selectivity and combinations thereof. This includes one or more chemical modifying agents (e.g. a reducing agent such as an amine), one or more physical processes (e.g. mechanical grinding at cryogenic temperatures also referred to as "cryo-grinding") and combinations of one or more chemical modifying agents and one or more physical processes. The term "cryo" in front of any treatment term refers to any treatment that occurs with cooling, under freezing temperatures, at cryogenic temperatures and any use of cryogenic fluids. Suitable cryogenic fluids include, but are not limited to for example, any conventional cryogens and other coolants such as chilled water, ice, compressible organic solvents such as freons, liquid carbon dioxide, liquid nitrogen, liquid helium and combinations thereof. Suitable chemical and physical modification of prepared (untreated) catalysts results in unexpected improvements in treated catalyst efficiency and selectivity in alkane, alkene or alkane and alkene oxidations as compared to corresponding untreated catalysts and improved yields of oxygenated products using modified catalysts using modified catalysts as compared to unmodified catalysts. The term prepared catalysts refers to unmodified catalysts. The prepared catalysts are obtained from commercial sources or are prepared by conventional preparative methods, including methods described herein. The term "treated catalysts" and "modified catalysts" does not refer to or include regenerated, reconditioned and recycled catalysts. The term conditioning refers to conventional heating of prepared metal oxide catalysts with gases including hydrogen, nitrogen, oxygen and selected combinations thereof.

As used herein, the term "cumulatively converting" refers producing a desired product stream from one or more specific reactants using one or more modified catalysts and modified catalyst systems of the invention under specific reaction conditions. As an illustrative embodiment, cumulatively converting an alkane to its corresponding unsaturated carboxylic acid means that the modified catalyst(s) utilized will produce a product stream comprising the unsaturated carboxylic acid corresponding to the added alkane when acting on a feed stream(s) comprising the alkane and molecular oxygen under the designated reaction conditions. According to a separate embodiment, the invention also provides a process for optimizing recycle conversion of specific alkanes, alkenes, alkanes and alkenes and their corresponding oxygenate products.

As used herein, mixed metal oxide catalyst refers to a catalyst comprising more than one metal oxide. The term "catalytic system" refers to two or more catalysts. For example, platinum metal and indium oxide impregnated on an alumina support defines both a catalytic system and a mixed metal oxide catalyst. Yet another example of both is palladium metal, vanadium oxide and magnesium oxide impregnated on silica.

Any one or more metal oxide catalysts are usefully modified and utilized in catalytic conversions of molecules containing carbon in accordance with the invention. According to one embodiment, the modified catalysts are modified mixed metal oxide catalysts useful for catalytically converting alkanes, alkenes and combinations of alkanes and alkenes to their corresponding oxygenates. The prepared metal oxide catalysts are modified using the one or more chemical, physical and combined chemical and physical treatments to provide modified metal oxide catalysts, including modified mixed metal oxide catalysts.

According to one embodiment of the invention, suitable prepared catalysts used and modified in accordance with the invention are one or more mixed metal oxide catalysts having a catalyst having the empirical formula

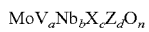

wherein X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, Y, rare earth elements and alkaline earth elements, $0.1 \leq a \leq 1.0$, $0.01 \leq b \leq 1.0$, $0.01 \leq c \leq 1.0$, $0 \leq d \leq 1.0$ and n is determined by the oxidation states of the other elements. Preparation of the mixed metal oxide (MMO) catalysts is described in U.S. Pat. Nos. 6,383,978; 6,641,996; 6,518,216; 6,403,525; 6,407,031; 6,407,280; and 6,589,907; U.S. Publication Application No. 20030004379; U.S. Provisional Application Ser. Nos. 60/235,977; 60/235,979; 60/235,981; 60/235,984; 60/235,983; 60/236,000; 60/236,073; 60/236,129; 60/236,143; 60/236,605; 60/236,250; 60/236,260; 60/236,262; 60/236,263; 60/283,245; and 60/286,218; and EP Patent Nos. EP 1 080 784; EP 1 192 982; EP 1 192 983; EP 1 192 984; EP 1 192 986; EP 1 192 987; EP 1 192 988; EP 1 192 982; EP 1 249 274; and EP 1 270 068. The synthesis of such MMO (mixed metal oxide) catalysts is accomplished by several methods well known by those having skill in the art. A precursor slurry of mixed metal salts is first prepared by conventional methods and methods described above that include, but are not limited to for example, rotary evaporation, drying under reduced pressure, hydrothermal methods, co-precipitation, solid-state synthesis, impregnation, incipient wetness, sol gel processing and combinations thereof. After the precursor slurry is prepared it is dried according to conventional drying methods including, but not limited to for example, drying in ovens, spray drying and freeze drying. The dried precursor is then calcined to obtain prepared MMO catalysts using well known techniques and techniques described above to those having skill in the art including, but not limited to for example, flow calcinations, static calcinations, rotary calcinations and fluid-bed calcinations. In some cases the prepared MMO catalysts are further milled to improve their catalytic activity.

It is noted that promoted mixed metal oxides having the empirical formulae $Mo_jV_mTe_nNb_yZ_zO_o$ or $W_jV_mTe_nNb_yZ_zO_o$, wherein Z, j, m, n, y, z connection with the present invention. Additional suitable embodiments are either of the aforesaid empirical formulae, wherein Z is Pd. Suitable solvents for the precursor solution include water; alcohols including, but not limited to, methanol, ethanol, propanol, and diols, etc.; as well as other polar solvents known in the art. Generally, water is preferred. The water is any water suitable for use in chemical syntheses including, without limitation, distilled water and de-ionized water. The amount of water present is preferably an amount sufficient to keep the elements substantially in solution long enough to avoid or minimize compositional and/or phase segregation during the preparation steps. Accordingly, the amount of water will vary according to the amounts and solubilities of the materials combined. Preferably, though lower concentrations of water are possible for forming a slurry, as stated above, the amount of water is sufficient to ensure an aqueous solution is formed, at the time of mixing.

According to a separate embodiment of the invention, suitable prepared mixed metal oxide catalysts used and modified in accordance with the invention are one or more promoted mixed metal oxide catalysts having the empirical formula $$J_jM_mN_nY_yZ_zO_o$$

wherein J is at least one element selected from the group consisting of Mo and W, M is at least one element selected from the group consisting of V and Ce, N is at least one element selected from the group consisting of Te, Sb and Se, Y is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, and Z is selected from the group consisting of Ni, Pd, Cu, Ag and Au; and wherein, when j=1, m=0.01 to 1.0, n=0.01 to 1.0, y=0.01 to 1.0, z=0.001 to 0.1 and o is dependent on the oxidation state of the other elements. Preparation of the mixed metal catalysts is described in U.S. Pat. Nos. 6,383,978; 6,641,996; 6,518,216; 6,403,525; 6,407,031; 6,407,280; and 6,589,907; U.S. Provisional Application Ser. Nos. 60/235,977; 60/235,979; 60/235,981; 60/235,984; 60/235,983; 60/236,000; 60/236,073; 60/236,129; 60/236,143; 60/236,605; 60/236,250; 60/236,260; 60/236,262; 60/236,263; 60/283,245; and 60/286,218; and EP Patent Nos. EP 1 080 784; EP 1 192 982; EP 1 192 983; EP 1 192 984; EP 1 192 986; EP 1 192 987; EP 1 192 988; EP 1 192 982; and EP 1 249 274.

According to a separate embodiment of the invention, suitable prepared catalysts modified and used in accordance with the invention are one or more mixed metal oxide catalysts having the empirical formula $$A_aD_bE_cX_dO_e$$

wherein A is at least one element selected from the group consisting of Mo and W, D is at least one element selected from the group consisting of V and Ce, E is at least one element selected from the group consisting of Te, Sb and Se, and X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Hf, Pb, P, Pm, Eu, Gd, Dy, Ho, Er, Tm, Yb and Lu; and a=1, b=0.01 to 1.0, c=0.01 to 1.0, d=0.01 to 1.0, and e is dependent on the oxidation state of the other elements. The catalyst composition is treated to exhibit peaks at X-ray diffraction angles (2θ) of 22.1°, 27.1°, 28.2°, 36.2°, 45.2°, and 50.0°, with a relative increase in a diffraction peak at the diffraction angle (2θ) of 27.1 degrees when compared with an untreated catalyst of like empirical formula.

In this regard, in addition to the above noted peak at 27.1 degrees, the preferred mixed metal oxide exhibits the following five main diffraction peaks at specific diffraction angles (2θ) in the X-ray diffraction pattern of the treated mixed metal oxide (as measured using Cu—Kα radiation as the source):

| X-ray lattice plane | | |
|---|---|---|
| Diffraction angle 2θ (±0.3°) | Spacing medium (Å) | Relative intensity |
| 22.1° | 4.02 | 100 |
| 28.2° | 3.16 | 20~150 |
| 36.2° | 2.48 | 5~60 |
| 45.2° | 2.00 | 2~40 |
| 50.0° | 1.82 | 2~40 |

The intensity of the X-ray diffraction peaks may vary upon the measuring of each crystal. However, the intensity, relative to the peak intensity at 22.1° being 100, is usually within the above ranges. Generally, the peak intensities at 2θ=22.1° and 28.2° are distinctly observed. However, so long as the above five diffraction peaks are observable, the basic crystal structure is the same even if other peaks are observed in addition to the five diffraction peaks (e.g. at 27.1 degrees), and such a structure is useful for the present invention. Preparation of the mixed metal catalysts is described in U.S. Patent Application Publication No. 20020183547 and European Patent Publication No. EP 1 249 274.

Other suitable prepared catalysts modified using the invention include those described in U.S. Pat. No. 5,380,933 discloses a method for producing an unsaturated carboxylic acid comprising subjecting an alkane to a vapor phase catalytic oxidation reaction in the presence of a catalyst containing a mixed metal oxide comprising, as essential components, Mo, V, Te, O and X, wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium; and wherein the proportions of the respective essential components, based on the total amount of the essential components, exclusive of oxygen, satisfy the following relationships: 0.25<r(Mo)<0.98, 0.003<r(V)<0.5, 0.003<r(Te)<0.5 and 0.003<r(X)<0.5, wherein r(Mo), r(V), r(Te) and r(X) are the molar fractions of Mo, V, Te and X, respectively, based on the total amount of the essential components exclusive of oxygen.

Yet other suitable examples of prepared catalysts modified using the invention include those described in Published International Application No. WO 00/29106 discloses a catalyst for selective oxidation of propane to oxygenated products including acrylic acid, acrolein and acetic acid, said catalyst system containing a catalyst composition comprising $$Mo_aV_bGa_cPd_dNb_eX_f$$

wherein X is at least one element selected from La, Te, Ge, Zn, Si, In and W,
a is 1,
b is 0.01 to 0.9,
c is >0 to 0.2,
d is 0.0000001 to 0.2,
e is >0 to 0.2, and
f is 0.0 to 0.5; and wherein the numerical values of a, b, c, d, e and f represent the relative gram-atom ratios of the elements Mo, V, Ga, Pd, Nb and X, respectively, in the catalyst and the elements are present in combination with oxygen.

Yet other suitable examples of prepared catalysts modified using the invention include those described in Japanese Laid-Open Patent Application Publication No. 2000-037623 and European Published Patent Application No. 0 630 879 B1. Other suitable catalysts for a variety of vapor phase oxidation reactions are described fully in U.S. Pat. Nos. 6,383,978, 6,403,525, 6,407,031, 6,407,280, 6,461,996, 6,472,552, 6,504,053, 6,589,907 and 6,624,111.

By way of an illustrative example, when a mixed metal oxide of the formula $Mo_aV_bTe_cNb_dO_e$ (wherein the element A is Mo, the element D is V, the element E is Te and the element X is Nb) is to be prepared, an aqueous solution of niobium oxalate and a solution of aqueous nitric acid may be added to an aqueous solution or slurry of ammonium heptamolybdate, ammonium metavanadate and telluric acid, so that the atomic ratio of the respective metal elements would be in the prescribed proportions. In one specific illustration, it is further contemplated that a 5% aqueous nitric acid is mixed with niobium oxalate solution in a ratio of 1:10 to 1.25:1 parts by volume acid solution to oxalate solution, and more preferably 1:5 to 1:1 parts by volume acid solution to oxalate solution.

For example, when a promoted mixed metal oxide of the formula $Mo_jV_mTe_nNb_yAu_zO_f$ wherein the element J is Mo, the element M is V, the element N is Te, the element Y is Nb, and the element Z is Au, is to be prepared, an aqueous solution of niobium oxalate may be added to an aqueous solution or slurry of ammonium heptamolybdate, ammonium metavanadate, telluric acid and ammonium tetrachloroaurate, so that the atomic ratio of the respective metal elements would be in the prescribed proportions.

A unmodified mixed metal oxide (promoted or not), thus obtained, exhibits excellent catalytic activities by itself. However, the unmodified mixed metal oxide is converted to a catalyst having higher activities by one or more chemical, physical and combinations of chemical and physical treatments.

Modified metal oxide catalysts are obtained by treating chemical, physical and combinations of chemical and physical treatments of suitable prepared metal oxide catalyst. Optionally, the modified catalysts are further modified by conventional processing techniques well known to persons having skill in this art.

Chemical treatments, resulting in treated/modified catalysts, include one or more chemical modifying agents. Suitable chemical modifying agents include, but are not limited to for example, oxidizing agents selected from hydrogen peroxide, nitrogen, nitric acid, nitric oxide, nitrogen dioxide, nitrogen trioxide, persulfate; reducing agents selected from amines, pyridine, hydrazine, quinoline, metal hydrides, sodium borohydride, C1-C4 alcohols, methanol, ethanol, sulfites, thiosulfites, aminothiols; combinations of oxidizing agents and reducing agents; acids selected from HCl, HNO3, H2SO4; organic acids, organic diacids, acetic acid, oxalic acid, combinations of C1-C4 alcohols and C1-C4 organic acids, oxalic acid and methanol; inorganic bases selected from NH3, NH4OH, H2NNH2, HONH2, NaOH, Ca(OH)2, CaO, Na2CO3, NaHCO3, organic bases selected from ethanol amine, diethanolamine, triethanolamine; pH adjustments; peroxides selected from inorganic peroxides, H2O2, organic peroxides, tBu2O2; chelating agents, ethylenediamine, ethylenediaminetetraacetic acid (EDTA); electrolysis including electrolytic reduction; treatment with high energy radiation including ultraviolet and X-ray radiation; and combinations thereof.

Physical treatments, resulting in treated/modified catalysts, include one or more physical processes. Suitable physical processes include, but are not limited to for example, cooling, cryogenic cooling, pressure cooling, compacting under pressure, high pressure die pressing, thermolyzing (also referred to as polymer burn off), mechanical grinding at cryogenic temperatures, high shear grinding at cryogenic temperatures, cryo-milling, cryo-densifying, cryo-stressing, cryo-fracturing, cryo-pelletizing, deforming, wash coating, molding, forming, shaping, casting, machining, laminating, drawing, extruding, lobalizing, impregnating, forming spheres (spherolizing or jetting), slurrying, cryo-slurrying, preparing shelled catalysts (shelling), multi-coating, electrolyzing, electrodepositing, compositing, foaming, cryo-fluidizing, cryo-spraying, thermal spraying, plasma spraying, vapor depositing, adsorbing, ablating, vitrifying, sintering, cryo-sintering, fusing, fuming, crystallizing, any altering of catalyst crystal structure, polycrystallizing, recrystallizing, any surface treating of the catalyst, any altering of catalyst surface structure, any altering of catalysts porosity, any altering of catalyst surface area, any altering of catalyst density, any altering of bulk catalysts structure, reducing the particle size of the primary catalyst particles in combination with cooling or thermolyzing the catalyst, and any combinations of chemical and physical treatments, including but not limited to solvent extraction, Soxhlet extraction, batch solvent extraction, continuous flow solvent extraction, extraction in supercritical solvents, contacting the catalyst with one or more leaching agents including solvents, altering catalyst pH, any chemical treatments used in modifying catalyst surface structure, mechanical grinding in supercritical solvents, chemisorbing one or more chemical agents, ultrasonification using one or more solvents selected from organic solvents such as alcohols and amines ultrasonification, and any physical treatments employing solvents under supercritical conditions. According to a separate embodiment, modified catalysts include one or more further chemical and/or physical treatments of already modified catalysts.

According to one embodiment, modified catalysts are further modified by one or more physical treatments including, but not limited to for example, heating, drying, cooling, freeze, pressure cooling, thermal die pressing, high pressure die pressing, thermal and high pressure die pressing, thermal high shear milling and grinding, thermal de-polymerizing, thermolyzing (also referred to as polymer burn off), mechanical grinding at cryogenic temperatures, mechanical grinding at elevated temperatures, thermal milling, cryo-milling, thermal shearing, cryo-shearing, cryo-densifying, densification, coagulation, flocculation, sedimenting, lyophilizing, agglomerating, reducing particle size of primary particles, increasing surface area of primary particles, thermal and cryo-compacting, thermal and cryo-compressing, thermal and cryo-stressing, cryo-fracturing, shear loading, thermal and cryo-shear loading, drawing, thermal and cryo-drawing, thermal and cryo-centrifuging, thermal and cryo-granulating, thermal and cryo-spray drying, atomizing, thermal and cryo-dry pressing, cryo-pressing, heat pressing, dry compacting, cryo-compacting, heat compacting, isocompacting, thermal and cryo-isocompacting, thermal and cryo-pelletizing, thermal and cryo-roll pressing, thermal and cryo-deforming, jiggering, thermal and cryo-molding, thermal and cryo-forming, thermal and cryo-shaping, thermal and cryo-casting, thermal and cryo-machining, thermal and cryo-laminating, thermal and cryo-tape casting, fiber drawing, thermal and cryo-fiber drawing, thermal and cryo-fiber extruding, thermal and cryo-extruding, thermal and cryo-lobalizing, thermal and cryo-impregnating, forming sphere forming (spherolizing or jetting), slurrying, cryo-slurrying, preparing shelled catalysts (shelling), multi-coating, electrolyzing, electrodepositing, compositing, rolling, roll forming, foaming, cementing, fluidizing, cryo-spraying, thermal spraying, plasma spraying, vapor depositing, adsorbing, ablating, firing, vitrifying, sintering, cryo-sintering, pre-shaping before extruding, thermal and cryo-pre-shaping before extruding, lobalizing, fusing, thermal fusing, fuming, coking, colloidalizing, crystallizing, thermal and cryo-crystallizing, any altering of crystal structure, polycrystallizing, recrystallizing, any surface treating, any altering of surface structure, any altering of porosity, any altering of density, any altering of bulk structure, altering catalyst pH, any chemical treatments used in modifying catalyst surface structure, mechanical grinding in supercritical solvents, chemisorbing one or more chemical agents, ultrasonification using one or more solvents selected from organic solvents, aqueous solvents and combinations of organic and aqueous solvents including, but limited to for example, acids, alcohols, chelating agents and amines ultrasonification, and any physical treatments employing solvents under supercritical conditions and any combinations thereof.

Other suitable treatments involve combinations of one or more chemical modifying agents and one or more physical processes, resulting in treated/modified catalysts. Suitable examples include, but are not limited to for example, solvent extraction using a Soxhlet extractor, extraction using a Parr bomb, solvent extraction using microwave radiation, batch solvent extraction, continuous flow solvent extraction, leaching, altering pH, any surface treatments, grinding in supercritical solvents, extraction in supercritical solvents, chemisorption, ultrasonification using one or more solvents selected from organic solvents such as alcohols and amines; and combinations thereof.

According to one embodiment of the invention, modified mixed metal oxides useful as catalysts in alkane oxidations are prepared by mechanical grinding unmodified (prepared) mixed metal oxide catalysts at cryogenic temperatures. Cryogenic temperatures are meant to refer to temperatures between 10° C. (283 K) to −269° C. (4 K). Catalysts are cryo-ground using a suitable cryogen source in combination with suitable corresponding milling equipment. Suitable examples include, but are not limited to for example, freeze milling using a freezer mill, and any milling at cryogenic temperatures. Such cryo-grinding affords modified mixed metal oxide catalysts and the resulting performance characteristics of the modified catalysts are improved selectivities and yields at constant alkane, alkene or alkane and alkene conversion. For example, cryo-milling mixed metal oxide catalysts having the empirical formula $$MoV_aNb_bX_cZ_dO_n$$

wherein X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, Y, rare earth elements and alkaline earth elements, $0.1 \leq a \leq 1.0$, $0.01 \leq b \leq 1.0$, $0.01 \leq c \leq 1.0$, $0 \leq d \leq 1.0$ and n is determined by the oxidation states of the other elements, provides modified mixed metal oxide catalysts whose catalytic performance results in significantly improved acrylic acid (AA) selectivities and yield at constant propane conversion as compared to corresponding unmodified mixed metal oxide catalysts or as compared to simply milling the corresponding unmodified mixed metal oxide catalysts using conventional mechanical grinding equipment.

According to a separate embodiment of the invention, modified mixed metal oxides useful as catalysts in alkane oxidations are prepared by treating corresponding unmodified (prepared) mixed metal oxide catalysts with one or more chemical modifying agents, namely one or more reducing agents. Suitable reducing agents include, for example, reducing agents selected from primary amines, secondary amine, tertiary amines, alkylamines, dialkylamines, trialkyl- and triaryl amines, methylamine, dimethylamine, trimethylamine, pyridine, hydrazine, quinoline, metal hydrides, sodium borohydride, C1-C4 alcohols, methanol, ethanol, sulfites, thiosulfites, aminothiols, combinations of oxidizing agents and reducing agents, NH3, NH4OH, H₂NNH2, HONH2, ethanol amine, diethanolamine, triethanolamine, adjusting to pH>7, electrolysis including electrolytic reduction and combinations thereof. Such post treatment affords modified mixed metal oxide catalysts and the resulting performance characteristics of the modified catalysts are improved selectivities and yields at constant alkane, alkene or alkane and alkene conversion. For example, modified mixed metal oxide catalysts having the empirical formula:

$$M_eMoV_aNb_bX_cZ_dO_n$$

wherein $M_e$ is at least one or more chemical modifying agents, X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, Y, rare earth elements and alkaline earth elements, $0.1 \leq a \leq 1.0$, $0.01 \leq b \leq 1.0$, $0.01 \leq c \leq 1.0$, $0 \leq d \leq 1.0$ and n, e are determined by the oxidation states of the other elements, using pyridine as a reducing agent results in significantly improved acrylic acid (AA) selectivities and yield at constant propane conversion as compared to corresponding unmodified mixed metal oxide catalysts.

According to a separate embodiment of the invention, modified mixed metal oxides useful as catalysts in alkane oxidations are prepared by a combination of cryo-grinding unmodified mixed metal oxide catalysts followed by solvent extraction of corresponding modified mixed metal oxide catalysts. Catalysts are cryo-ground using a suitable cryogen source in combination with suitable corresponding milling equipment. Suitable examples include, but are not limited to for example, freeze milling using a freezer mill, and any milling at cryogenic temperatures. Extraction of the modified metal catalysts is subsequently performed using conventional extraction equipment, including for example Soxhlet extractors or Parr bomb extractors using suitable organic solvents, aqueous solvents and combinations of organic and aqueous solvents. Suitable organic solvents include for example C1-C4 alcohols, combinations of C1-C4 alcohols and C1-C6 organic acids/diacids and combinations of C1-C4 alcohols and C1-C6 organic bases. Suitable aqueous solvents include, but are not limited to for example, acids, bases chelating agents and combinations thereof. The combination of cryo-grinding followed by solvent extraction affords modified mixed metal oxide catalysts and the resulting performance characteristics of the modified catalysts are improved selectivities and yields at constant alkane, alkene or alkane and alkene conversion. For example, cryo-milling mixed metal oxide catalysts having the empirical formula $$MoV_aNb_bX_cZ_dO_n$$

wherein X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, Y, rare earth elements and alkaline earth elements, $0.1 \leq a \leq 1.0$, $0.01 \leq b \leq 1.0$, $0.01 \leq c \leq 1.0$, $0 \leq d \leq 1.0$ and n is determined by the oxidation states of the other elements, followed by solvent extraction of the corresponding modified catalysts results in significantly improved acrylic acid (AA) selectivities and yield at constant propane conversion as compared to corresponding unmodified mixed metal oxide catalysts or as compared to simply grinding the corresponding unmodified mixed metal oxide catalysts using conventional mechanical grinders.

Solvent extraction is carried out in a batch process or using continuous solvent flow extraction. Modified catalyst particles are slurried in to an extraction medium comprising one or more organic solvents, typical alcohols. Other organic solvents are also usefully employed. The extraction process is carried out for deliberate periods of time in conventional equipment including for example a Soxhlet extractor, a Parr bomb reactor heated to a suitable temperature and pressure, heated by convection or using microwave radiation. One characteristic of both types of solvent extractions is that the catalyst particles are in constant contact with the extraction solvent. As the extraction process proceeds with time, the concentration of dissolved materials extracted into solvent increases until a chemical equilibrium is reached. One advantage of continuous solvent flow extraction is that the catalyst particles are not in contact with the bulk of the solvent. Dissolved or extracted materials accumulate in the bulk solvent vessel and evaporation and condensation of the solvent insures a solvent containing no dissolved material for extraction. The continuous solvent flow extraction method is carried out in open systems at atmospheric pressure or closed systems under pressure. Furthermore, there is no need for washing the catalyst particles with additional new solvents after extraction nor is there the need for filtration in order to separate the catalysts particles from the extraction solvent. Suitable extraction solvents include but are not limited to single phase solvents. Suitable solvents include for example water, C1-C4 alcohols, C1-C6 organic acids and diacids, C1-C6 amines, chelating agents and combinations thereof.

According to a separate embodiment of the invention, modified mixed metal oxides useful as catalysts in alkane oxidations are prepared by a combination of ultrasonification of unmodified mixed metal oxide catalysts in one or more organic solvents, aqueous solvents and combinations of organic and aqueous solvents. In a related separate embodiment, ultrasonifaction is combined with solvent extraction of corresponding modified mixed metal oxide catalysts. Catalysts are milled ultrasonically using conventional ultrasonfication equipment. The ultrasonicator is equipped with a cryogen source and a heating source. Extraction of the modified metal catalysts is subsequently performed using conventional extraction equipment, including for example Soxhlet extractors using suitable organic solvents. Suitable organic solvents include for example C1-C4 alcohols, combinations of C1-C4 alcohols and C1-C6 organic acids/diacids, combinations of C1-C4 alcohols and one or more chelating agents, combinations of C1-C4 alcohols and C1-C6 organic bases and corresponding combinations thereof. Ultrasonification in one or more solvents and the combination of ultrasonification followed by solvent extraction affords modified mixed metal oxide catalysts whose catalytic performance characteristics results in improved selectivities and yield at constant propane conversion as compared to corresponding unmodified mixed metal oxide catalysts or as compared to simply grinding the corresponding unmodified mixed metal oxide catalysts using conventional mechanical grinders.

According to a separate embodiment of the invention, modified mixed metal oxides useful as catalysts in alkane oxidations are prepared by densifying the catalysts by pressure compacting or cryo-milling. Catalysts are pressure compacted using conventional compaction equipment. The pressure compactor is optionally equipped with a cryogen source and a heating source. Compaction of catalysts under compacting loads affords modified mixed metal oxide catalysts and the resulting performance characteristics of the modified catalysts are improved selectivities and yield at constant propane conversion as compared to corresponding unmodified mixed metal oxide catalysts. Modified MMO catalysts exhibit higher AA yields as compared to unmodified MMO catalysts. For example, a 0.2 to 0.3 g/cm$^3$ increase in catalyst density increases AA yield up 5%. Cryo-grinding was found to provide an 0.15 to 0.20 g/cm$^3$ increase in packed density of selected modified MMO catalysts. In another example, AA yields from higher density cryo-milled modified MMO catalysts were 2-4% (absolute) higher. Surface area data of selected modified MMO catalysts have higher surface areas (13 m$^2$/g) as compared to unmodified and conventionally milled MMO catalysts (6 to 11 m$^2$/g), accounting for the AA yield increase.

According to a separate embodiment of the invention, modified mixed metal oxides useful as catalysts in alkane oxidations are prepared by a combination of solvent extraction of unmodified mixed metal oxide catalysts in one or more supercritical solvents. In a related separate embodiment, a modified catalyst as compared with conventional preparation is prepared under supercritical conditions. Conventional equipment is used to create supercritical solvent conditions. Suitable examples of supercritical solvents include, but are no limited to for example, CO2, H2O, NH3, CH3OH and ethanol. The supercritical solvent modified catalysts are optionally solvent extracted or further processed using conventional techniques described herein. Supercritical solvent extraction of the modified metal catalysts is subsequently performed using conventional supercritical extraction equipment using suitable organic solvents. Suitable organic solvents include for example, water, carbon dioxide, ammonia, C1-C4 alcohols, combinations of C1-C4 alcohols and C1-C6 organic acids/diacids and combinations of C1-C4 alcohols and C1-C6 organic bases. Supercritical modification of MMO catalysts in one or more solvents and the combination of supercritical solvent extraction followed by affords further modification including, but not limited to heating and milling of the modified mixed metal oxide catalysts and the resulting catalytic performance characteristics of the modified catalysts are improved selectivities and yield at constant propane conversion as compared to corresponding unmodified mixed metal oxide catalysts or as compared to simply grinding the corresponding unmodified mixed metal oxide catalysts using conventional mechanical grinding equipment.

According to a separate embodiment, unmodified MMO catalysts are treated with a source of NO$_x$. In a preferred embodiment, the treatment is performed by further admixing the precursor admixture with a fluid for introducing NO$_x$ to the precursor admixture and then drying or calcining the resulting admixture. Accordingly, preferably the fluid includes a NO$_x$ source such as nitric acid, ammonium nitrate, ammonium nitrite, NO, NO$_2$ or a mixture thereof. More preferably, the fluid is a liquid, such as an aqueous solution, including the NO$_x$ source dissolved or dispersed therein. In another embodiment, it is contemplated that a gas including a source of NO$_x$ is bubbled or otherwise introduced into the precursor admixture for treating the admixture. For example, the precursor admixture prior to calcination is prepared by mixing the precursor admixture and nitric acid solution to form a resulting admixture having 0.01 to 20 percent by weight of nitric acid, and more preferably 0.05 to 10 percent by weight of nitric acid. In another example, the resulting admixture has 0.1 to 1.5 percent by weight of nitric acid. Alternatively expressed, prior to calcination, preferably the nitric acid is present in an amount of at least 500 ppm of the admixture, more preferably, at least 1500 ppm. An example of a preferred range of concentrations includes 1000 to 15,000 ppm nitric acid.

In another embodiment, where the source of NO$_x$ includes NO$_2$, the amount of NO$_2$ ranges from 500 to 12,000 ppm and more preferably 1000 to 9000 ppm.

Once the resulting modified or treated catalysts are formed, liquid therein is removed by any suitable method, known in the art, for forming a catalyst precursor. Such methods include, without limitation, vacuum drying, freeze drying, spray drying, rotary evaporation and air-drying. Vacuum drying is generally performed at pressures ranging from 10 mm Hg to 500 mm Hg. Freeze drying typically entails freezing the slurry or solution, using, for instance, liquid nitrogen, and drying the frozen slurry or solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mm Hg to 760 mm Hg, preferably at a bath temperature of from 40° to 90° C. and at a pressure of from 10 mm Hg to 350 mm Hg, more preferably at a bath temperature of from 40° C. to 60° C. and at a pressure of from 10 mm Hg to 40 mm Hg. Air drying may be effected at temperatures ranging from 25° C. to 90° C. Rotary evaporation or air-drying are generally preferred.

Once obtained, the resulting modified catalyst precursor is used as modified or is further modified by conventional processes well known in the art, including further milling and calcining.

According to one embodiment, calcination may be conducted in an oxygen-containing atmosphere or in the substantial absence of oxygen, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst or may not flow thereover (a static environment). When the inert atmosphere does flow over the surface of the catalyst precursor, the flow rate can vary over a wide range, e.g., at a space velocity of from 1 to 500 hr$^{-1}$.

Calcination of both unmodified and modified catalysts is usually performed at a temperature of from 350° C. to 850° C., preferably from 400° C. to 700° C., more preferably from 500° C. to 640° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired promoted mixed metal oxide.

According to one embodiment, the unmodified and modified catalyst is calcined in two stages. In the first stage, the catalyst precursor is calcined in an oxidizing environment (e.g. air) at a temperature of from 200° C. to 400° C., preferably from 275° C. to 325° C. for from 15 minutes to 8 hours, preferably for from 1 to 3 hours. In the second stage, the material from the first stage is calcined in a non-oxidizing environment (e.g., an inert atmosphere) at a temperature of from 500° C. to 700° C., preferably for from 550° C. to 650° C., for 15 minutes to 8 hours, preferably for from 1 to 3 hours. Optionally, a reducing gas, such as, for example, ammonia or hydrogen, may be added during the second stage calcination.

According to a separate embodiment, a modified metal oxide catalyst is obtained through cryo-grinding (also referred to a freeze milling). There is no particular restriction as to the grinding method, and conventional methods may be employed. As a dry grinding method, a method of using a gas stream grinder may, for example, be mentioned wherein coarse particles are permitted to collide with one another in a high speed gas stream for grinding. The grinding may be conducted not only mechanically but also by using a mortar or the like in the case of a small scale operation.

As a wet grinding method wherein grinding is conducted in a wet state by adding water or an organic solvent to the above mixed metal oxide, a conventional method of using a rotary cylinder-type medium mill or a medium-stirring type mill, may be mentioned. The rotary cylinder-type medium mill is a wet mill of the type wherein a container for the object to be ground is rotated, and it includes, for example, a ball mill and a rod mill. The medium-stirring type mill is a wet mill of the type wherein the object to be ground, contained in a container is stirred by a stirring apparatus, and it includes, for example, a rotary screw type mill, and a rotary disc type mill.

The conditions for grinding may suitably be set to meet the nature of the above-mentioned promoted mixed metal oxide, the viscosity, the concentration, etc. of the solvent used in the case of wet grinding, or the optimum conditions of the grinding apparatus. However, it is preferred that grinding is conducted until the average particle size of the ground catalyst precursor would usually be at most 20 µm, more preferably at most 5 µm. Improvement in the catalytic performance occurs due to such cryo-grinding.

Further, in some cases, it is possible to further improve catalytic activities by further adding a solvent to the ground catalyst precursor to form a solution or slurry, followed by drying again. There is no particular restriction as to the concentration of the solution or slurry, and it is usual to adjust the solution or slurry so that the total amount of the starting material compounds for the ground catalyst precursor is from 10 to 60 wt. %. Then, this solution or slurry is dried by a method such as spray drying, freeze drying, evaporation to dryness or vacuum drying, preferably by the spray drying method. Further, similar drying may be conducted also in the case where wet grinding is conducted.

The modified mixed metal oxide (promoted or not) obtained by the above-mentioned method may be used as a final catalyst, but it may further be subjected to one or more additional chemical, physical and combinations of chemical and physical treatments. According to one embodiment, modified catalysts are further modified using heat treatment. As an exemplary embodiment, heat treatment usually is performed at a temperature of from 200° to 700° C. for from 0.1 to 10 hours.

The resulting modified mixed metal oxide (promoted or not) may be used by itself as a solid catalyst. The modified catalysts are also combined with one or more suitable carriers, such as, without limitation, silica, alumina, titania, aluminosilicate, diatomaceous earth or zirconia, according to art-disclosed techniques. Further, it may be processed to a suitable shape or particle size using art disclosed techniques, depending upon the scale or system of the reactor.

Alternatively, the metal components of the modified catalysts are supported on materials such as alumina, silica, silica-alumina, zirconia, titania, etc. by conventional incipient wetness techniques. In one typical method, solutions containing the metals are contacted with the dry support such that the support is wetted; then, the resultant wetted material is dried, for example, at a temperature from room temperature to 200° C. followed by calcination as described above. In another method, metal solutions are contacted with the support, typically in volume ratios of greater than 3:1 (metal solution:support), and the solution agitated such that the metal ions are ion-exchanged onto the support. The metal-containing support is then dried and calcined as detailed above.

According to a separate embodiment, modified catalysts are also prepared using one or more promoters. The starting materials for the above promoted mixed metal oxide are not limited to those described above. A wide range of materials including, for example, oxides, nitrates, halides or oxyhalides, alkoxides, acetylacetonates, and organometallic compounds may be used. For example, ammonium heptamolybdate may be utilized for the source of molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, ammonium metavanadate may be utilized for the source of vanadium in the catalyst. However, compounds such as $V_2O_5$, $V_2O_3$, $VOCl_3$, $VCl_4$, $VO(OC_2H_5)_3$, vanadium acetylacetonate and vanadyl acetylacetonate may also be utilized instead of ammonium metavanadate. The tellurium source may include telluric acid, $TeCl_4$, $Te(OC_2H_5)_5$, $Te(OCH(CH_3)_2)_4$ and $TeO_2$. The niobium source may include ammonium niobium oxalate, $Nb_2O_5$, $NbCl_5$, niobic acid or $Nb(OC_2H_5)_5$ as well as the more conventional niobium oxalate.

In addition, with reference to the promoter elements for the promoted catalyst, the nickel source may include nickel (II) acetate tetrahydrate, $Ni(NO_3)_2$, nickel(II) oxalate, NiO, $Ni(OH)_2$, $NiCl_2$, $NiBr_2$, nickel(II) acetylacetonate, nickel(II) sulfate, NiS or nickel metal. The palladium source may include $Pd(NO_3)_2$, palladium(II) acetate, palladium oxalate, PdO, $Pd(OH)_2$, $PdCl_2$, palladium acetylacetonate or palladium metal. The copper source may be copper acetate, copper acetate monohydrate, copper acetate hydrate, copper acetylacetonate, copper bromide, copper carbonate, copper chloride, copper chloride dihydrate, copper fluoride, copper formate hydrate, copper gluconate, copper hydroxide, copper iodide, copper methoxide, copper nitrate, copper nitrate hydrate, copper oxide, copper tartrate hydrate or a solution of copper in an aqueous inorganic acid, e.g., nitric acid. The silver source may be silver acetate, silver acetylacetonate, silver benzoate, silver bromide, silver carbonate, silver chloride, silver citrate hydrate, silver fluoride, silver iodide, silver lactate, silver nitrate, silver nitrite, silver oxide, silver phosphate or a solution of silver in an aqueous inorganic acid, e.g., nitric acid. The gold source may be ammonium tetrachloroaurate, gold bromide, gold chloride, gold cyanide, gold hydroxide, gold iodide, gold oxide, gold trichloride acid and gold sulfide.

Modified catalysts of the invention have different chemical, physical and performance characteristics in catalytic reactions of carbon based molecules as compared to unmodified catalysts. According to one embodiment, the treated catalyst exhibits changes in X-ray lines, peak positions and intensity of such lines and peaks as compared with corresponding X-ray diffraction data for corresponding unmodified catalysts. Such difference indicate structural differences between the modified and unmodified catalysts and are born out in the catalytic activity and selectivity. For example, compared with an untreated catalyst composition, a treated catalyst composition of the present invention exhibits an X-ray diffraction pattern having a relative increase in a diffraction peak at a diffraction angle (2θ) of 27.1 degrees when compared with an untreated catalyst, which may exhibit no peak at all at 27.1 degrees.

The relative difference between peak intensities of treated versus untreated compositions may be greater than 5%, more preferably greater than 10%, and still more preferably greater than 20% of the intensity of the untreated catalyst composition at the diffraction angle (2θ) of 27.1 degrees. Without intending to be bound by theory, it is believed that at least two phases (A and B) are present in the resulting mixed metal oxide catalyst and the treatment of the catalyst precursor with a source of $NO_x$ results in an increase in phase B relative to phase A in the resulting catalyst. The increase in phase B is believed to contribute to improved performance of the catalyst in terms of selectivity, reactivity and yield.

Modified catalysts of the invention exhibit improved catalyst performance characteristics selected from the group consisting of optimized catalyst properties, yields of oxygenates including unsaturated carboxylic acids, from their corresponding alkanes, alkenes or combinations of corresponding alkanes and alkenes at constant alkane/alkene conversion, selectivity of oxygenate products, including unsaturated carboxylic acids, from their corresponding alkanes, alkenes or combinations of corresponding alkanes and alkenes, optimized feed conversion, cumulative yield of the desired oxidation product, optimized reactant/product recycle conversion, optimized product conversion via recycle and combinations thereof, as compared to the unmodified catalyst.

Modified catalysts of the invention have improved performance characteristics as compared to unmodified catalysts in catalytic processes comprising any carbon containing molecule. According to one embodiment of the invention, the modified catalysts have improved performance characteristics as compared to unmodified catalysts in processes for preparing dehydrogenated products and oxygenated products from alkanes and oxygen, alkenes and oxygen and combination of alkanes, alkenes and oxygen. The reactions are typically carried out in conventional reactors with the alkanes catalytically converted at conventional residence times (>100 milliseconds) in conventional reactors. According to a separate embodiment the reactions are carried out at short contact times (≦100 milliseconds) in a short contact time reactor. Suitable alkanes include alkanes having straight or branched chains. Examples of suitable alkanes are $C_2$-$C_{25}$ alkanes, including $C_2$-$C_8$ alkanes such as propane, butane, isobutane, pentane, isopentane, hexane and heptane. Particularly preferred alkanes are propane and isobutane.

Modified catalysts of the invention convert alkanes, alkenes or alkanes and alkenes to their corresponding alkenes and oxygenates including saturated carboxylic acids, unsaturated carboxylic acids, esters thereof, and higher analogue unsaturated carboxylic acids and esters thereof. The modified catalyst and catalytic systems are designed to provide specific alkenes, oxygenates and combinations thereof. Alkanes are catalytically converted to one or more products in a single pass, including corresponding alkenes. Any unreacted alkane, alkene or intermediate is recycled to catalytically convert it to its corresponding oxygenate. According to one embodiment, alkenes produced from dehydrogenation of corresponding alkanes using catalyst systems of the invention are deliberately produced as in-process chemical intermediates and not isolated before selective partial oxidation to oxygenated products. For example, when catalytically converting an alkane to its corresponding ethylenically unsaturated carboxylic acid, any unreacted alkene produced is recovered or recycled to catalytically convert it to its corresponding ethylenically unsaturated carboxylic acid product stream.

According to a separate embodiment, alkanes, alkenes or alkanes and alkenes are also catalytically converted to its corresponding oxygenates through two or more catalytic zones. For example, an alkane is catalytically converted to its corresponding saturated carboxylic acid in a first catalytic zone or layer of a mixed catalyst bed. The saturated carboxylic acid, in the presence of an additional formaldehyde stream, to its corresponding higher analogue ethylenically unsaturated carboxylic acid in a second catalytic zone or layer of a mixed bed catalyst. In a specific example, propane is catalytically converted to propionic acid and the propionic acid in the presence of formaldehyde is catalytically converted to methacrylic acid.

As used herein, the term "higher analogue unsaturated carboxylic acid" and "ester of a higher analogue unsaturated carboxylic acid" refer to products having at least one additional carbon atom in the final product as compared to the alkane or alkene reactants. For example given above, propane ($C_3$ alkane) is converted to propionic acid ($C_3$ saturated carboxylic acid), which in the presence of formaldehyde is converted to its corresponding higher analogue ($C_4$) carboxylic acid, methacrylic acid using catalysts of the invention.

Suitable alkenes used in the invention include alkenes having straight or branched chains. Examples of suitable alkenes include $C_2$-$C_{25}$ alkenes, preferably $C_2$-$C_8$ alkenes such as propene (propylene), 1-butene (butylene), 2-methylpropene (isobutylene), 1-pentene and 1-hexene. Particularly preferred alkenes are propylene and isobutylene.

Suitable aldehydes used in the invention include for example formaldehyde, ethanal, propanal and butanal.

Modified catalysts and catalyst systems of the invention convert alkanes, alkenes or alkanes and alkenes to their corresponding oxygenates including saturated carboxylic acids having straight or branched chains. Examples include $C_2$-$C_8$ saturated carboxylic acids such as propionic acid, butanoic acid, isobutyric acid, pentanoic acid and hexanoic acid. According to one embodiment, saturated carboxylic acids produced from corresponding alkanes using catalyst systems of the invention are deliberately produced as in-process chemical intermediates and not isolated before selective partial oxidation to oxygenated products including unsaturated carboxylic acids, esters of unsaturated carboxylic acids, and higher esters of unsaturated carboxylic acids. According to a separate embodiment, any saturated carboxylic acid produced is converted using catalysts of the invention to its corresponding product stream including an ethylenically unsaturated carboxylic acid, esters thereof, a higher analogue unsaturated carboxylic acid or esters thereof.

Modified catalysts and catalyst systems of the invention also convert alkanes to their corresponding ethylenically unsaturated carboxylic acids and higher analogues having straight or branched chains. Examples include $C_2$-$C_8$ ethylenically unsaturated carboxylic acids such as acrylic acid, methacrylic acid, butenoic acid, pentenoic acid, hexenoic acid, maleic acid, and crotonic acid. Higher analogue ethylenically unsaturated carboxylic acids are prepared from corresponding alkanes and aldehydes. For example, methacrylic acid is prepared from propane and formaldehyde. According to a separate embodiment, the corresponding acid anhydrides are also produced when preparing ethylenically unsaturated carboxylic acids from their respective alkanes. The modified catalysts of the invention are usefully employed to convert propane to arcylic acid and its higher unsaturated carboxylic acid methacrylic acid and to convert isobutane to methacrylic acid.

The modified catalysts and catalyst systems of the invention are also advantageously utilized converting alkanes to their corresponding esters of unsaturated carboxylic acids and higher analogues. Specifically, these esters include, but are not limited to, butyl acrylate from butyl alcohol and propane, β-hydroxyethyl acrylate from ethylene glycol and propane, methyl methacrylate from methanol and isobutane, butyl methacrylate from butyl alcohol and isobutane, β-hydroxyethyl methacrylate from ethylene glycol and isobutane, and methyl methacrylate from propane, formaldehyde and methanol.

In addition to these esters, other esters are formed through this invention by varying the type of alcohol introduced into the reactor and/or the alkane, alkene or alkane and alkene introduced into the reactor.

Suitable alcohols include monohydric alcohols, dihydric alcohols and polyhydric alcohols. Of the monohydric alcohols reference may be made, without limitation, to $C_1$-$C_{20}$ alcohols, preferably $C_1$-$C_6$ alcohols, most preferably $C_1$-$C_4$ alcohols. The monohydric alcohols may be aromatic, aliphatic or alicyclic; straight or branched chain; saturated or unsaturated; and primary, secondary or tertiary. Particularly preferred monohydric alcohols include methyl alcohol, ethyl alcohol, propyl alcohol, isopropyl alcohol, butyl alcohol, isobutyl alcohol and tertiary butyl alcohol. Of the dihydric alcohols reference may be made, without limitation, to $C_2$-$C_6$ diols, preferably $C_2$-$C_4$ diols. The dihydric alcohols may be aliphatic or alicyclic; straight or branched chain; and primary, secondary or tertiary. Particularly preferred dihydric alcohols include ethylene glycol (1,2-ethanediol), propylene glycol (1,2-propanediol), trimethylene glycol (1,3-propanediol), 1,2-butanediol and 2,3-butanediol. Of the polyhydric alcohols reference will only be made to glycerol (1,2,3-propanetriol).

The unsaturated carboxylic acid corresponding to the added alkane is the α,β-unsaturated carboxylic acid having the same number of carbon atoms as the starting alkane and the same carbon chain structure as the starting alkane, e.g., acrylic acid is the unsaturated carboxylic acid corresponding to propane and methacrylic acid is the unsaturated carboxylic acid corresponding to isobutane.

Similarly, the unsaturated carboxylic acid corresponding to an alkene is the α,β-unsaturated carboxylic acid having the same number of carbon atoms as the alkene and the same carbon chain structure as the alkene, e.g., acrylic acid is the unsaturated carboxylic acid corresponding to propene and methacrylic acid is the unsaturated carboxylic acid corresponding to isobutene.

Likewise, the unsaturated carboxylic acid corresponding to an unsaturated aldehyde is the α,β-unsaturated carboxylic acid having the same number of carbon atoms as the unsaturated aldehyde and the same carbon chain structure as the unsaturated aldehyde, e.g., acrylic acid is the unsaturated carboxylic acid corresponding to acrolein and methacrylic acid is the unsaturated carboxylic acid corresponding to methacrolein.

The alkene corresponding to the added alkane is the alkene having the same number of carbon atoms as the starting alkane and the same carbon chain structure as the starting alkane, e.g., propene is the alkene corresponding to propane and isobutene is the alkene corresponding to isobutane. (For alkenes having four or more carbon atoms, the double bond is in the 2-position of the carbon-carbon chain of the alkene.) The unsaturated aldehyde corresponding to the added alkane is the α,β-unsaturated aldehyde having the same number of carbon atoms as the starting alkane and the same carbon chain structure as the starting alkane, e.g., acrolein is the unsaturated aldehyde corresponding to propane and methacrolein is the unsaturated carboxylic acid corresponding to isobutane.

Similarly, the unsaturated aldehyde corresponding to an alkene is the α,β-unsaturated carboxylic acid having the same number of carbon atoms as the alkene and the same carbon chain structure as the alkene, e.g., acrolein is the unsaturated aldehyde corresponding to propene and methacrolein is the unsaturated aldehyde corresponding to isobutene.

The modified catalysts are processed in to three-dimensional forms or are supported on three-dimensional support structures.

The support structure is three-dimensional, i.e. the support has dimensions along an x, y and z orthogonal axes of a Cartesian coordinate system, and affords a relatively high surface area per unit volume. Though lower and higher amounts are possible, in one embodiment, the support structure exhibits a surface area of 0.01 to 50 $m^2/g$, preferably 0.1 to 10 $m^2/g$.

Preferably, the support structure will have a porous structure and exhibit a pore volume percent ranging from 1 to 95%, more preferably 5 to 80%, and still more preferably 10 to 50%. Thus, the support structure permits relatively high feed velocities with insubstantial pressure drop.

Further, the support structure is sufficiently strong so that it does not fracture under the weight of the catalyst, which can range up to almost 100% of the weight of the combination of the catalyst and the support structure. More preferably, however, the support structure is at least 60% of the weight of the combination. Still more preferably, it is 70 to 99.99% of the weight of the combination. Even still more preferably, the support structure is 90 to 99.9% of the weight of the combination.

The exact physical form of the support structure is not particularly important so long as it meets the above noted general criteria. Examples of suitable physical forms of modified catalysts and supported modified catalysts include foam, honeycomb, lattice, mesh, monolith, woven fiber, non-woven fiber, gauze, perforated substrates (e.g., foil), particle compacts, fibrous mat and mixtures thereof. For these supports it will be appreciated that typically one or more open cells will be included in the structure. The cell size may vary as desired, as may the cell density, cell surface area, open frontal area and other corresponding dimensions. By way of example, one such structure has an open frontal area of at least 75%. The cell shape may also vary and may include polygonal shapes, circles, ellipses, as well as others.

The support structure may be fabricated from a material that is inert to the reaction environment of the catalytic reaction. Suitable materials include ceramics and their isomorphs such as silica, alumina (including α-, β- and γ-isomorphs), silica-alumina, aluminosilicate, zirconia, titania, boria, mullite, lithium aluminum silicate, oxide-bonded silicon carbide, metal alloy monoliths, Fricker type metal alloys, FeCrAl alloys and mixtures thereof. (Alternatively, the catalyst may be prepared so as to define the support structure itself, e.g., by "green" compacting or another suitable technique.)

The modified catalysts may be applied to the support structure using any suitable art-disclosed technique. For instance, the catalyst may be vapor deposited (e.g., by sputtering, plasma deposition or some other form of vapor deposition). The catalyst may be impregnated or coated thereon (e.g., by wash coating a support with a solution, slurry, suspension or dispersion of catalyst). The support may be coated with a catalyst powder (i.e. powder coating). (Alternatively, where the support structure is the catalyst itself, a "green" body of catalyst may be compacted to yield the desired structure.)

Modified catalysts of the invention include promoters, modifiers and oxidants. Promoters are usefully employed to oxidatively dehydrogenate alkanes to their corresponding alkenes. According to one embodiment the modified catalysts also incorporate finely dispersed metal particles including alloys (microns to nanometers) having high surface area. Alternatively, the modified catalyst is in the form of a fine gauze, including nanometer sized wires. The catalyst is impregnated on the support using techniques selected from metal sputtering, chemical vapor deposition, chemical and/or electrochemical reduction of the metal oxide.

Modifiers are usefully employed to partially oxidize alkanes to their corresponding saturated carboxylic acids and unsaturated carboxylic acids. Typical modifiers are metal oxide and MMO catalysts in the form of binary, ternary, quaternary or higher order mixed metal oxides. The modifier may preferably be present in an amount of from 0.0001 to 10 wt % of the catalyst composition (promoter plus reducible metal oxide), more preferably from 0.001 to 5 wt % of the catalyst composition, and still more preferably from 0.01 to 2 wt % of the catalyst composition.

Oxidants are usefully employed to partially oxidize alkanes, alkenes and alkanes and alkenes to their corresponding alkenes, saturated carboxylic acids and unsaturated carboxylic acids. Typically they are also metal oxide catalysts and MMO catalysts in the form of binary, ternary, quaternary or higher order mixed metal oxides. The promoter is typically present in an amount of from 0.0001 to 10 wt % of the catalyst composition (promoter plus reducible metal oxide), more preferably from 0.001 to 5 wt % of the catalyst composition, and still more preferably from 0.01 to 2 wt % of the catalyst composition. The modified catalyst is present alone or deposited, including impregnated, on the support in the form of finely dispersed metal oxide particles (microns to nanometers) having high surface area. The catalytic system component comprises metal oxides and metal oxides used in combination with promoters in contact with a metal oxide supported.

The unmodified catalysts are prepared in steps. In a first step, a slurry or solution may be formed by admixing metal compounds, preferably at least one of which contains oxygen, and at least one solvent in appropriate amounts to form the slurry or solution. Preferably, a solution is formed at this stage of the catalyst preparation. Generally, the metal compounds contain the elements required for the particular catalyst, as previously defined.

Suitable solvents include water, alcohols including, but not limited to, methanol, ethanol, propanol, and diols, etc., as well as other polar solvents known in the art. Generally, water is preferred. The water is any water suitable for use in chemical syntheses including, without limitation, distilled water and de-ionized water. The amount of water present is preferably an amount sufficient to keep the elements substantially in solution long enough to avoid or minimize compositional and/or phase segregation during the preparation steps. Accordingly, the amount of water will vary according to the amounts and solubilities of the materials combined. However, as stated above, the amount of water is preferably sufficient to ensure an aqueous solution is formed at the time of mixing.

For example, when a mixed metal oxide of the formula $Mo_aV_bTe_cNb_dO_e$ is to be prepared, an aqueous solution of telluric acid, an aqueous solution of niobium oxalate and a solution or slurry of ammonium paramolybdate may be sequentially added to an aqueous solution containing a predetermined amount of ammonium metavanadate, so that the atomic ratio of the respective metal elements would be in the prescribed proportions.

Once the aqueous slurry or solution (preferably a solution) is formed, the water is removed by any suitable method, known in the art, to form a catalyst precursor. Such methods include, without limitation, vacuum drying, freeze drying, spray drying, rotary evaporation and air drying. Vacuum drying is generally performed at pressures ranging from 10 mmHg to 500 mmHg. Freeze drying typically entails freezing the slurry or solution, using, for instance, liquid nitrogen, and drying the frozen slurry or solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mmHg to 760 mmHg, preferably at a bath temperature of from 400° to 90° C. and at a pressure of from 10 mmHg to 350 mmHg, more preferably at a bath temperature of from 40° C. to 60° C. and at a pressure of from 10 mmHg to 40 mmHg. Air drying may be effected at temperatures ranging from 25° C. to 90° C. Rotary evaporation or air drying are generally employed.

Once obtained, the catalyst precursor is calcined. The calcination is usually conducted in an oxidizing atmosphere, but it is also possible to conduct the calcination in a non-oxidizing atmosphere, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 $hr^{-1}$.

The calcination is usually performed at a temperature of from 350° C. to 1000° C., including from 400° C. to 900° C., and including from 500° C. to 800° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired mixed metal oxide.

In one mode of operation, the catalyst precursor is calcined in two stages. In the first stage, the catalyst precursor is calcined in an oxidizing atmosphere (e.g., air) at a temperature of from 200° C. to 400° C., including from 275° C. to 325° C. for from 15 minutes to 8 hours, including from 1 to 3 hours. In the second stage, the material from the first stage is calcined in a non-oxidizing environment (e.g., an inert atmosphere) at a temperature of from 500° C. to 900° C., including from 550° C. to 800° C., for from 15 minutes to 8 hours, including from 1 to 3 hours.

Optionally, a reducing gas, such as, for example, ammonia or hydrogen, is added during the second stage calcination.

In a separate mode of operation, the catalyst precursor in the first stage is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

Although any type of heating mechanism, e.g., a furnace, may be utilized during the calcination, it is preferred to conduct the calcination under a flow of the designated gaseous environment. Therefore, it is advantageous to conduct the calcination in a bed with continuous flow of the desired gas(es) through the bed of solid catalyst precursor particles.

With calcination, a mixed metal oxide catalyst is formed having a stoichiometric or non-stoichiometric amounts of the respective elements.

The invention provides also process for preparing modified mixed metal oxide catalysts that convert alkanes to their corresponding alkenes and oxygenates comprising the steps of:

mixing salts of metals selected from the group consisting of Mo, Te, V, Ta and Nb at temperatures above the melting point of the highest melting salt to form a miscible molten salt; and calcining the mixture of salts in the presence of oxygen to provide a mixed metal oxide catalyst, optionally using a metal halide salt or a metal oxyhalide salt as solvent.

The starting materials for the above mixed metal oxide are not limited to those described above. A wide range of materials including, for example, oxides, nitrates, halides or oxyhalides, alkoxides, acetylacetonates and organometallic compounds may be used. For example, ammonium heptamolybdate may be utilized for the source of molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, ammonium metavanadate may be utilized for the source of vanadium in the catalyst. However, compounds such as $V_2O_5$, $V_2O_3$, $VOCl_3$, $VCl_4$, $VO(OC_2H_5)_3$, vanadium acetylacetonate and vanadyl acetylacetonate may also be utilized instead of ammonium metavanadate. The tellurium source may include telluric acid, $TeCl_4$, $Te(OC_2H_5)_5$, $Te(OCH(CH_3)_2)_4$ and $TeO_2$. The niobium source may include ammonium niobium oxalate, $Nb_2O_5$, $NbCl_5$, niobic acid or $Nb(OC_2H_5)_5$ as well as the more conventional niobium oxalate.

Use of low-melting salts opens up a new approach to preparing mixed metal oxide catalysts. The advantages over current aqueous suspension methods include higher incorporation of sparsely soluble metal salts, better control of metal ratios, and more homogeneous catalyst systems. One unique approach is to use low-melting halides of the desired MMO metals to prepare salt solutions. Variations of this approach are discussed below in more detail.

Halide salts of the desired metals are combined by mixing at temperatures above the melting point of the highest melting salt. The molten salts should be miscible with each other forming a stable, homogeneous solution of molten salt.

One advantage of the method is that it eliminates the solubility limits inherent in aqueous slurry systems. By using molten salts, we can incorporate much higher levels of such metals as niobium, vanadium, and palladium, the salts of which have relatively low solubilities in aqueous media. Examples of metal salts and their melting points are given in Table 4. These salts are readily available, relatively inexpensive, and have reasonably low melting points.

According to one embodiment, certain metal oxyhalides are useful as solvents in preparing metal oxides using the method. Vanadium halides such as vanadium tetrachloride, $VCl_4$ and vanadyl trichloride ($VOCl_3$), which are liquids at room temperature and are ideal solvents for the chloride salts of the other metals because of their polarity and low boiling points (BP(VCl$_4$)=148° C., BP(VOCl$_3$)=127° C.). Metal halides are dissolved in one of these solvents in the desired mole ratios, and then excess vanadium is removed via evaporation under reduced pressure and inert atmosphere. The catalyst cake is then calcined under O$_2$/Argon to liberate oxides of chlorine, generating the mixed metal oxide catalyst. Alternatively, the catalyst cake can be calcined under wet Argon to generate the mixed metal oxide (MMO) catalyst and HCl. In addition, mixed metal halides (MMH) are also converted to MMO, discussed in more detail below.

According to a separate embodiment, it is advantageous to introduce oxygen earlier in the synthesis. This is achieved by mixing metal oxides into either the molten salt solution or the VCl$_4$/VOCl$_3$ solution. This method reduces the amount of chlorine that must be removed during calcination and generates mixed oxychloride precursors that already have some of the desired characteristics of the final catalyst. One preparation is to dissolve oxides of niobium, tellurium, and molybdenum in VCl$_4$/VOCl$_3$. The resulting precursor will already have high oxygen content.

According to a separate embodiment, mixed metal halides (MMH) are also converted to MMO. Three methods for converting mixed metal halides (MMH) and mixed metal oxyhalides (MMOH) to mixed metal oxides (MMO) are described:

(A) MMH precursors are calcined under wet (1%) argon at elevated temperatures (600° C.). The off-gas is scrubbed with caustic to trap the product HCl.

(B) MMH precursors are calcined under argon with low O$_2$ concentration. The low O$_2$ concentration moderates the reaction. The oxychloride gases is scrubbed with caustic.

(C) MMH precursors are chemically converted to the metal alkoxides under mild conditions, followed by calcination under O$_2$/Argon to generate the MMO catalyst. By using the alkoxide intermediate, the crystalline structure of the final catalyst can be altered.

The MMO prepared from the molten salt method can be prepared on support materials including metal oxide supports. One advantage of using molten salt or salt solutions in VCl$_4$/VOCl$_3$ is that it is comparatively easy to impregnate support material, such as alumina, zirconia, silica, or titanium oxide, and allows the use of either the pearl technique or sequential loading. The relatively high metal concentrations in solution enables one to increase the metal loading on the support material, providing an ideal catalyst for millisecond contact time reactions.

Alternatively, another approach to preparing supported MMO catalyst is addition of finely-divided support material such as aluminum oxide into the salt solution (molten salt or VCl$_4$/VOCl$_3$ solution) to create a suspension/slurry. After concentration and calcination, the final catalyst prepared is a supported MMO catalyst with significantly higher surface area.

A mixed metal oxide, thus obtained, exhibits excellent catalytic activities by itself. However, the mixed metal oxide can be converted to a catalyst having higher activities by grinding.

There is no particular restriction as to the grinding method, and conventional methods may be employed. As a dry grinding method, a method of using a gas stream grinder may, for example, be mentioned wherein coarse particles are permitted to collide with one another in a high speed gas stream for grinding. The grinding may be conducted not only mechanically but also by using a mortar or the like in the case of a small scale operation.

As a wet grinding method wherein grinding is conducted in a wet state by adding water or an organic solvent to the above mixed metal oxide, a conventional method of using a rotary cylinder-type medium mill or a medium-stirring type mill, may be mentioned. The rotary cylinder-type medium mill is a wet mill of the type wherein a container for the object to be ground is rotated, and it includes, for example, a ball mill and a rod mill. The medium-stirring type mill is a wet mill of the type wherein the object to be ground, contained in a container is stirred by a stirring apparatus, and it includes, for example, a rotary screw type mill, and a rotary disc type mill.

The conditions for grinding may suitably be set to meet the nature of the above-mentioned mixed metal oxide; the viscosity, the concentration, etc. of the solvent used in the case of wet grinding; or the optimum conditions of the grinding apparatus. However, it is preferred that grinding is conducted until the average particle size of the ground catalyst precursor would usually be at most 20 μm, more preferably at most 5 μm. Improvement in the catalytic performance may be brought about by such grinding.

Further, in some cases, it is possible to further improve the catalytic activities by further adding a solvent to the ground catalyst precursor to form a solution or slurry, followed by drying again. There is no particular restriction as to the concentration of the solution or slurry, and it is usual to adjust the solution or slurry so that the total amount of the starting material compounds for the ground catalyst precursor is from 10 to 60 wt %. Then, this solution or slurry is dried by a method such as spray drying, freeze drying, evaporation to dryness or vacuum drying. Further, similar drying may be conducted also in the case where wet grinding is conducted.

The oxide obtained by the above-mentioned method may be used as a final catalyst, but it may further be subjected to heat treatment usually at a temperature of from 200° to 800° C. for from 0.1 to 10 hours.

The mixed metal oxide thus obtained is typically used by itself as a solid catalyst, but may be formed into a catalyst together with a suitable carrier such as silica, alumina, titania, aluminosilicate, diatomaceous earth or zirconia. Further, it may be molded into a suitable shape and particle size depending upon the scale or system of the reactor. Alternatively, the metal components of the modified catalysts may be supported on materials such as alumina, silica, silica-alumina, zirconia, titania, etc. by conventional incipient wetness techniques. In one typical method, solutions containing the metals are contacted with the dry support such that the support is wetted; then, the resultant wetted material is dried, for example, at a temperature from room temperature to 200° C. followed by calcination as described above. In another method, metal solutions are contacted with the support, typically in volume ratios of greater than 3:1 (metal solution:support), and the solution agitated such that the metal ions are ion-exchanged onto the support. The metal containing support is then dried and calcined as detailed above.

When using a catalyst system including two or more modified catalysts, the catalyst may be in the form of a physical blend of the several catalysts. Preferably, the concentration of the catalysts may be varied so that the first catalyst component will have a tendency to be concentrated at the reactor inlet while subsequent catalysts will have a tendency to be concentrated in sequential zones extending to the reactor outlet. Most preferably, the catalysts will form a layered bed (also referred to a mixed bed catalyst), with the first catalyst component forming the layer closest to the reactor inlet and the subsequent catalysts forming sequential layers to the reactor outlet. The layers abut one another or may be separated from one another by a layer of inert material or a void space.

The invention provides a process for producing an unsaturated carboxylic acid, which comprises subjecting an alkane, alkene or a mixture of an alkane and an alkene ("alkane/alkene"), to a vapor phase catalytic oxidation reaction in the presence of a catalyst containing the above promoted mixed metal oxide, to produce an unsaturated carboxylic acid.

In the production of such an unsaturated carboxylic acid, it is preferred to employ a starting material gas that contains steam. In such a case, as a starting material gas to be supplied to the reaction system, a gas mixture comprising a steam-containing alkane, or a steam-containing mixture of alkane and alkene, and an oxygen-containing gas, is usually used. However, the steam-containing alkane, or the steam-containing mixture of alkane and alkene, and the oxygen-containing gas may be alternately supplied to the reaction system. The steam to be employed may be present in the form of steam gas in the reaction system, and the manner of its introduction is not particularly limited.

Further, as a diluting gas, an inert gas such as nitrogen, argon or helium may be supplied. The molar ratio (alkane or mixture of alkane and alkene):(oxygen):(diluting gas):($H_2O$) in the starting material gas is preferably (1):(0.1 to 10):(0 to 20):(0.2 to 70), more preferably (1):(1 to 5.0):(0 to 10):(5 to 40).

When steam is supplied together with the alkane, or the mixture of alkane and alkene, as starting material gas, the selectivity for an unsaturated carboxylic acid is distinctly improved, and the unsaturated carboxylic acid can be obtained from the alkane, or mixture of alkane and alkene, in good yield simply by contacting in one stage. However, the conventional technique utilizes a diluting gas such as nitrogen, argon or helium for the purpose of diluting the starting material. As such a diluting gas, to adjust the space velocity, the oxygen partial pressure and the steam partial pressure, an inert gas such as nitrogen, argon or helium may be used together with the steam.

As the starting material alkane it is preferred to employ a $C_{2-8}$ alkane, particularly propane, isobutane or n-butane; more preferably, propane or isobutane; most preferably, propane. According to the present invention, from such an alkane, an unsaturated carboxylic acid such as an α,β-unsaturated carboxylic acid can be obtained in good yield. For example, when propane or isobutane is used as the starting material alkane, acrylic acid or methacrylic acid will be obtained, respectively, in good yield.

In the present invention, as the starting material mixture of alkane and alkene, it is preferred to employ a mixture of $C_{2-8}$ alkane and $C_{2-8}$ alkene, particularly propane and propene, isobutane and isobutene or n-butane and n-butene. As the starting material mixture of alkane and alkene, propane and propene or isobutane and isobutene are more preferred. Most preferred is a mixture of propane and propene. According to the present invention, from such a mixture of an alkane and an alkene, an unsaturated carboxylic acid such as an α,β-unsaturated carboxylic acid can be obtained in good yield. For example, when propane and propene or isobutane and isobutene are used as the starting material mixture of alkane and alkene, acrylic acid or methacrylic acid will be obtained, respectively, in good yield. Preferably, in the mixture of alkane and alkene, the alkene is present in an amount of at least 0.5% by weight, more preferably at least 1.0% by weight to 95% by weight; most preferably, 3% by weight to 90% by weight.

As an alternative, an alkanol, such as isobutanol, which will dehydrate under the reaction conditions to form its corresponding alkene, i.e. isobutene, may also be used as a feed to the present process or in conjunction with the previously mentioned feed streams.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the oxidation reaction of the present invention is not clearly understood, but the oxidation reaction is carried out by oxygen atoms present in the above mixed metal oxide or by molecular oxygen present in the feed gas. To incorporate molecular oxygen into the feed gas, such molecular oxygen may be pure oxygen gas. However, it is usually more economical to use an oxygen-containing gas such as air, since purity is not particularly required.

It is also possible to use only an alkane, or a mixture of alkane and alkene, substantially in the absence of molecular oxygen for the vapor phase catalytic reaction. In such a case, it is preferred to adopt a method wherein a part of the catalyst is appropriately withdrawn from the reaction zone from time to time, then sent to an oxidation regenerator, regenerated and then returned to the reaction zone for reuse. As the regeneration method of the catalyst, a method may, for example, be mentioned which comprises contacting an oxidative gas such as oxygen, air or nitrogen monoxide with the catalyst in the regenerator usually at a temperature of from 300° to 600° C.

This aspect present invention is described in still further detail with respect to a case where propane is used as the starting material alkane and air is used as the oxygen source. The reaction system may be preferably a fixed bed system. The proportion of air to be supplied to the reaction system is important for the selectivity for the resulting acrylic acid, and it is usually at most 25 moles, preferably from 0.2 to 18 moles per mole of propane, whereby high selectivity for acrylic acid can be obtained. This reaction can be conducted usually under atmospheric pressure, but may be conducted under a slightly elevated pressure or slightly reduced pressure. With respect to other alkanes such as isobutane, or to mixtures of alkanes and alkenes such as propane and propene, the composition of the feed gas may be selected in accordance with the conditions for propane.

Typical reaction conditions for the oxidation of propane or isobutane to acrylic acid or methacrylic acid may be utilized in the practice of the present invention. The process may be practiced in a single pass mode (only fresh feed is fed to the reactor) or in a recycle mode (at least a portion of the reactor effluent is returned to the reactor). General conditions for the process of the present invention are as follows: the reaction temperature can vary from 200° C. to 700° C., but is usually in the range of from 200° C. to 550° C., more preferably 250° C. to 480° C., most preferably 300° C. to 400° C.; the gas space velocity, SV, in the vapor phase reaction is usually within a range of from 100 to 10,000 hr$^{-1}$, preferably 300 to 6,000 hr$^{-1}$, more preferably 300 to 2,000 hr$^{-1}$; the average contact time with the catalyst can be from 0.01 to 10 seconds or more, but is usually in the range of from 0.1 to 10 seconds, preferably from 0.2 to 6 seconds; the pressure in the reaction zone usually ranges from 0 to 75 psig, but is preferably no more than 50 psig. In a single pass mode process, it is preferred that the oxygen be supplied from an oxygen-containing gas such as air. The single pass mode process may also be practiced with oxygen addition. In the practice of the recycle mode process, oxygen gas by itself is the preferred source so as to avoid the build up of inert gases in the reaction zone. The feed of hydrocarbon in the catalytic process is dependent on the mode of operation (e.g. single pass, batch, recycle, etc.) and ranges from 2 wt. % to 50 wt. %. According to a separate embodiment, the catalytic process is a batch process. According to a separate process, the catalytic process is run continuously. The catalytic process all conventional beds including, but not limited to static fluid beds, fluidized beds, moving beds, transport beds, moving beds such as rising and ebulating beds. Any catalytic process is carried out under steady state conditions or non steady state conditions.

Of course, in the oxidation reaction of the present invention, it is important that the hydrocarbon and oxygen concentrations in the feed gases be maintained at the appropriate levels to minimize or avoid entering a flammable regime within the reaction zone or especially at the outlet of the reactor zone. Generally, it is preferred that the outlet oxygen levels be low to both minimize after-burning and, particularly, in the recycle mode of operation, to minimize the amount of oxygen in the recycled gaseous effluent stream. In addition, operation of the reaction at a low temperature (below 450° C.) is extremely attractive because after-burning becomes less of a problem which enables the attainment of higher selectivity to the desired products. The catalyst of the present invention operates more efficiently at the lower temperature range set forth above, significantly reducing the formation of acetic acid and carbon oxides, and increasing selectivity to acrylic acid. As a diluting gas to adjust the space velocity and the oxygen partial pressure, an inert gas such as nitrogen, argon or helium may be employed.

When the oxidation reaction of propane, and especially the oxidation reaction of propane and propene, is conducted by the method of the present invention, carbon monoxide, carbon dioxide, acetic acid, etc. may be produced as by-products, in addition to acrylic acid. Further, in the method of the present invention, an unsaturated aldehyde may sometimes be formed depending upon the reaction conditions. For example, when propane is present in the starting material mixture, acrolein may be formed; and when isobutane is present in the starting material mixture, methacrolein may be formed. In such a case, such an unsaturated aldehyde can be converted to the desired unsaturated carboxylic acid by subjecting it again to the vapor phase catalytic oxidation with the promoted mixed metal oxide-containing catalyst of the present invention or by subjecting it to a vapor phase catalytic oxidation reaction with a conventional oxidation reaction catalyst for an unsaturated aldehyde.

Turning now in more specific detail to another aspect of the present invention, the method comprises subjecting an alkane, or a mixture of an alkane and an alkene, to a vapor phase catalytic oxidation reaction with ammonia in the presence of a catalyst containing the above mixed metal oxide, to produce an unsaturated nitrile.

In the production of such an unsaturated nitrile, as the starting material alkane, it is preferred to employ a $C_{2-8}$ alkane such as propane, butane, isobutane, pentane, hexane and heptane. However, in view of the industrial application of nitriles to be produced, it is preferred to employ a lower alkane having 3 or 4 carbon atoms, particularly propane and isobutane.

Similarly, as the starting material mixture of alkane and alkene, it is preferred to employ a mixture of $C_{2-8}$ alkane and $C_{2-8}$ alkene such as propane and propene, butane and butene, isobutane and isobutene, pentane and pentene, hexane and hexene, and heptane and heptene. However, in view of the industrial application of nitriles to be produced, it is more preferred to employ a mixture of a lower alkane having 3 or 4 carbon atoms and a lower alkene having 3 or 4 carbon atoms, particularly propane and propene or isobutane and isobutene. Preferably, in the mixture of alkane and alkene, the alkene is present in an amount of at least 0.5% by weight, more preferably at least 1.0% by weight to 95% by weight, most preferably 3% by weight to 90% by weight.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

According to a separate embodiment, a short contact reactor is employed with the one or more modified catalysts of the invention. The short contact time reactor is of a type suitable for the use of a fixed catalyst bed in contact with a gaseous stream of reactants. For instance, a shell and tube type of reactor may be utilized, wherein one or more tubes are packed with catalyst(s) so as to allow a reactant gas stream to be passed in one end of the tube(s) and a product stream to be withdrawn from the other end of the tube(s). The tube(s) being disposed in a shell so that a heat transfer medium may be circulated about the tube(s).

In the case of the utilization of a single catalyst or catalyst system, the gas stream comprising the alkane, molecular oxygen and any additional reactant feeds including but not limited to alkenes, oxygen, air, hydrogen, carbon monoxide, carbon dioxide, formaldehyde and alcohols, steam and any diluents including nitrogen, argon may all be fed into the front end(s) of the tube(s) together. Alternatively, the alkane and the molecular oxygen-containing gas may be fed into the front end(s) of the tube(s) while the additional reactants, steam and diluents may be fed (also referred to as staging) into the tube(s) at a predetermined downstream location (typically chosen so as to have a certain minimum concentration of product alkene present in the gas stream passing through the tube(s), e.g., 3%, preferably 5%, most preferably 7%).

In the case of the utilization of catalyst systems including two or more catalysts, e.g., a first catalyst component and a second catalyst component as described above, once again the gas stream comprising the alkane, the oxygen-containing gas and any additional reactant feeds including but not limited to alkenes, oxygen, air, hydrogen, carbon monoxide, carbon dioxide, formaldehyde and alcohols, steam and any diluents including nitrogen, argon are fed to the front end(s) of the tube(s) together. Alternatively, and preferably, the alkane and the molecular oxygen-containing gas are staged into the front end(s) of the tube(s) while any additional reactant feeds, steam and diluents are staged into the tube(s) at a predetermined downstream location (typically chosen so at have a certain minimum concentration of desired product present in the gas stream passing through the tube(s), as set forth above; or in the case of the utilization of layered beds of catalyst, as described above, intermediate two layered catalyst beds).

Typical reaction conditions for the oxidation of propane or isobutane to acrylic acid or methacrylic acid including respective esters thereof which are utilized in the practice of the present invention include: reaction temperatures which can vary from 300° C. to 1000° C., but are usually in the range of flame temperatures (from 500° C. to 1000° C.); the average contact time with the catalyst (i.e. the reactor residence time) is not more than 100 milliseconds, including not more than 80 milliseconds, and including not more than 50 milliseconds; the pressure in the reaction zone usually ranges from 0 to 75 psig, including no more than 50 psig.

The invention provides a process for preparing unsaturated carboxylic acids from corresponding alkanes, the process comprising the step of: providing one or more modified catalysts cumulatively effective at converting the gaseous alkane to its corresponding gaseous unsaturated carboxylic acid;

wherein the second catalyst layer is separated at a distance downstream from the first catalyst layer and the reactor is operated at a temperature of from 100° C. to 700° C., with a reactor residence time of no less than 100 milliseconds. As a separate embodiment, a short contact time reactor is operated at a temperature of from 100° C. to 700° C., with a reactor residence time of than 100 or less milliseconds. 300° C. to 400° C., with a second reaction zone residence time of no greater than 100 milliseconds;

It is preferred to pass a gaseous stream comprising propane or isobutane and molecular oxygen to the reactor. In addition, the feed may contain an additional reactant, adjuvant such as steam or a diluent such as an inert gas, e.g., nitrogen, argon or carbon dioxide.

In a separate embodiment, the gaseous stream of the alkane is passed through the reactor in a single pass or wherein any unreacted alkane is recycled back into the gaseous stream of alkane entering the reactor and any saturated carboxylic acid is recycled back into the second catalyst zone to increase the overall yield of unsaturated carboxylic acid.

The invention also provides a process comprising the steps of: (a) converting an alkane to its corresponding products selected from alkene, unsaturated carboxylic acid, and higher analogue unsaturated carboxylic acid in a short contact time reactor using the catalyst systems of the invention; and (b) adding the resulting product or products to the front end of a second fixed bed oxidation reactor with the product(s) from the first reactor acting as feed to the second reactor. For example, propane is converted to propylene using a catalyst system as described in a short contact time reactor. The propylene is then fed to second oxidation reactor that converts its to acrylic acid. According to one embodiment this includes feeding any unreacted alkane from the first reactor to the second reactor to recycle the alkane. For example, any unreacted propane is recycled to the first SCTR or added as a feed to the second oxidation reactor. The second oxidation reactor comprises any conventional industrial scale oxidation reactor used for converting alkenes to unsaturated carboxylic acids at longer residence times (seconds). Alternatively, the second oxidation reactor comprises a second SCTR operating at millisecond residence times.

Any source of molecular oxygen may be employed in this process, e.g., oxygen, oxygen-enriched gases or air. Air may be the most economical source of oxygen, especially in the absence of any recycle.

The invention also provides a process for the production of esters of unsaturated carboxylic acids, the process comprising the step of:

passing a gaseous alkane, molecular oxygen and a gaseous alcohol to a short contact time reactor, the reactor including a mixed catalyst bed comprising (a) a first catalyst layer comprising one or more modified catalysts cumulatively effective at converting the gaseous alkane to its corresponding gaseous unsaturated carboxylic acid; wherein the catalysts of the first layer are impregnated on a metal oxide support; and (b) a second catalyst layer comprising one or more unmodified or modified catalysts cumulatively effective at converting the gaseous unsaturated carboxylic acid to its corresponding gaseous ester;

wherein the second catalyst layer is separated at a distance downstream from the first catalyst layer and the reactor is operated at a one or more temperatures of from 100° C. to 1000° C. In a separate embodiment the modified catalysts are partitioned into one or more zones, the first reaction zone being operated at a temperature of from 100° C. to 1000° C., the second reaction zone being operated at a temperature of from 300° C. to 400° C. The second catalyst comprises one or more unmodified or modified superacids.

According to yet another embodiment, provides a process for catalytically converting alkanes to their corresponding higher unsaturated carboxylic acids and then catalytically converting them to their corresponding esters in the presence of specific alcohols.

The second catalyst comprises one or more modified or umodified superacid. A superacid, according to the definition of Gillespie, is an acid that is stronger than 100% sulfuric acid, i.e. it has a Hammett acidity value $H_0 < -12$. Representative superacids include, but are not limited to: zeolite supported $TiO_2/(SO_4)_2$, $(SO_4)_2/ZrO_2$—$TiO_2$, $(SO_4)_2/ZrO_2$—$Dy_2O_3$, $(SO_4)_2/TiO_2$, $(SO_4)_2/ZrO_2$—$NiO$, $SO_4/ZrO_2$, $SO_4/ZrO_2Al_2O_3$, $(SO_4)_2/Fe_2O_3$, $(SO_4)_2/ZrO_2$, $C_4F_9SO_3H$—$SbF_5$, $CF_3SO_3H$—$SbF_5$, Pt/sulfated zirconium oxide, $HSO_3F$—$SO_2ClF$, $SbF_5$—$HSO_3F$—$SO_2ClF$, $MF_5/AlF_3$ (M=Ta, Nb, Sb), $B(OSO_2CF_3)_3$, $B(OSO_2CF_3)_3$—$CF_3SO_3H$, $SbF_5$—$SiO_2$—$Al_2O_3$, $SbF_5$—$TiO_2$—$SiO_2$ and $SbF_5$—$TiO_2$. Preferably, solid superacids are utilized, e.g., sulfated oxides, supported Lewis acids and supported liquid superacids. Only a small number of oxides produce superacid sites on sulfation, including $ZrO_2$, $TiO_2$, $HfO_2$, $Fe_2O_3$ and $SnO_2$. The acid sites are generated by treating an amorphous oxyhydrate of these elements with $H_2SO_4$ or $(NH_4)_2SO_4$ and calcining the products at temperatures of 500° C.-650° C. During the calcination, the oxides are transformed into a crystalline tetragonal phase, which is covered by a small number of sulfate groups. $H_2MoO_4$ or $H_xWO_4$ may also be used to activate the oxide.

In a separate embodiment of the present invention, an alcohol is reacted with an unsaturated aldehyde to form an acetal. Such reaction can be carried out by contacting the aldehyde with an excess of the anhydrous alcohol in the presence of a small amount of an anhydrous acid, e.g., anhydrous HCl. Preferably, the aldehyde and the alcohol can be passed through a bed containing an acid catalyst, e.g., through a bed of a strongly acidic ion exchange resin, such as Amberlyst 15.

The so-formed acetal and molecular oxygen are fed to a reactor containing at least one catalyst effective for the oxidation of the acetal to its corresponding ester. Examples of such a catalyst include well known Pd and Bi on alumina or V oxides.

The modified catalysts of the invention are usefully employed in catalytic processes described in a pending provisional U.S. application (Ser. No. 06/000,000). The application provides a process which addresses the problem of a decreased total yield of oxidation product in multi-stage vapor phase oxidation reactions which employ staged oxygen arrangements for conversion of lower alkanes and alkenes, and mixtures thereof, to unsaturated carboxylic acids and/or unsaturated nitrites. More particularly, it has been discovered that in such processes, the removal of at least a portion of the oxidation product from each intermediate effluent stream, for example, by inter-stage partial condensation, prior to adding more oxygen and feeding the effluent stream to the next stage, unexpectedly results in overall cumulative oxidation product yields greater than either the original single-stage system or the system including only staged oxygen arrangements.

The present invention provides an improved process for the production of unsaturated carboxylic acids and unsaturated nitrites from their corresponding $C_2$-$C_8$ alkanes, or mixtures of $C_2$-$C_8$ alkanes and alkenes, that utilizes a multi-stage reaction system and includes the steps of separating the oxidation product from one or more intermediate effluent streams, as well as feeding additional oxygen to reaction zones subsequent to the first reaction zone.

The process using modified catalysts of the invention is for producing unsaturated carboxylic acids or unsaturated nitrites by vapor phase oxidation reaction of their corresponding $C_2$-$C_8$ alkanes, $C_2$-$C_8$ alkenes, and mixtures thereof. The process of the present invention uses a reaction system, having at least two reaction zones arranged in series with one another and at least one catalyst capable of catalyzing the vapor phase oxidation reaction disposed in each of the at least two reaction zones. Furthermore, at least one intermediate effluent stream exits a preceding one of the at least two reaction zones and is at least partially fed to a subsequent one of the at least two reaction zones. The process of the present invention comprises separating the at least one intermediate effluent stream into at least an intermediate product stream comprising an oxidation product selected from the group consisting of an unsaturated carboxylic acid and an unsaturated nitrile, and an intermediate feed stream comprising starting materials selected from the group consisting of an unreacted $C_2$-$C_8$ alkane, an unreacted $C_2$-$C_8$ alkene, and mixtures thereof; feeding the intermediate feed stream to the subsequent reaction zone; and feeding an oxygen-containing gas to the subsequent reaction zone. In one alternative embodiment, two or more of the reaction zones may be contained within a single reactor vessel.

The separating step may be performed by cooling the at least one intermediate effluent stream such that at least a portion of the oxidation products condenses out of the at least one intermediate effluent stream. Such cooling may be achieved with a condenser. The separating step may, alternatively, be performed using an absorber.

In a particular application of the present invention, the $C_2$-$C_8$ alkane, $C_2$-$C_8$ alkene, or mixture thereof may comprise propane, propene, or a mixture thereof, and the oxidation product may comprise acrylic acid.

The process also comprises feeding ammonia-containing gas to each of the at least two reaction zones. In a particular application of the process, in which ammonia-containing gas is fed to each of the at least two reaction zones, the $C_2$-$C_8$ alkane, $C_2$-$C_8$ alkene, or mixture thereof, may comprise propane, propene, or a mixture thereof, and the oxidation product may comprise acrylonitrile.

Separators suitable for use with the present invention include any suitable fluid separator capable of separating a gaseous product stream into multiple streams according to composition, such as separating a gaseous output stream into a first stream containing primarily the desired reaction product(s) and a second stream containing primarily unreacted materials and by-products. For example, while not intending to be limited, the separator may be a partial condenser 16, 20, such as a conventional heat exchanger, capable of cooling the gaseous output stream sufficiently to condense and separate out at least a portion of the lowest boiling point components of the gaseous output stream would be suitable for use with the process 10 of the present invention. The coolant in such a condenser may be, for example, without limitation, cooling tower water having a temperature between 85° F. and 105° F. (29° C. to 40° C.), or chilled water having a temperature between 32° F. and 40° F. (0° C. and 5° C.). In addition, for example, the separators may include gas absorbers or gas adsorbers.

Suitable starting materials, which are discussed hereinafter and which are readily determinable by persons having ordinary skill in the art, are fed into the first reaction zone 12. In the first reaction zone 12, the starting materials come into contact with the catalyst and react with one another to form the desired oxidation products, as well as various side products and by-products, according to the particular types of $C_2$ to $C_5 8$ alkanes and alkenes used.

Suitable starting materials for the process 10 of the present invention depend upon the desired oxidation product and typically include, but are not limited to, a $C_2$ to $C_8$ alkane, a $C_2$ to $C_8$ alkene, or a mixture thereof, and an oxygen-containing gas, as well as, optionally, steam, diluting gases and ammonia. The starting materials may be added separately and simultaneously to the first reaction zone 12, or they may be mixed and fed to the first reaction zone 12 as one or more combined streams. For example, as explained in further detail hereinafter, the initial feed stream 22, shown in FIG. 1, may be a combined stream comprising an oxygen-containing gas and a $C_2$ to $C_8$ alkane, a $C_2$ to $C_8$ alkene, or a mixture thereof. The optional supplemental streams 24, 24', 24", shown in phantom in FIG. 1, may be, for example, steam-containing gases or ammonia-containing gases, depending upon the particular oxidation products desired. The optional supplemental streams 24, 24', 24" may even comprise additional $C_2$ to $C_8$ alkane, $C_2$ to $C_8$ alkene, or a mixture thereof.

The detailed mechanism of the oxidation reaction of the present invention is not clearly understood, but the oxidation reaction is carried out by oxygen atoms present in the above mixed metal oxide or by molecular oxygen present in the feed gas. Addition of oxygen-containing gas to the starting materials provides such molecular oxygen to the reaction system. The term "oxygen-containing gas," as used herein, refers to any gas comprising from 0.01% up to 100% oxygen, including, for example, air. Thus, although the oxygen-containing gas may be pure oxygen gas, it is usually more economical to use an oxygen-containing gas such as air, since purity is not particularly required.

The purity of the starting material, i.e., the $C_2$ to $C_8$ alkane, the $C_2$ to $C_8$ alkene, or the mixture thereof, is not particularly limited. Thus, commercial grades of such alkanes, or mixtures of such alkanes and alkenes, may be used as starting material for the process 10 of the present invention, although higher purities are advantageous from the standpoint of minimizing competing side reactions. In addition, mixed $C_2$ to $C_8$ alkane/alkene feeds are generally more easily obtained and may include price incentives (e.g., lower separation costs) relative to pure $C_2$ to $C_8$ alkane feeds. For example, a mixture of alkane and alkene containing a lower alkene such as ethene, a lower alkane such as methane or ethane, air or carbon dioxide, as impurities, may be used without any particular problem. Further, the starting material mixture of $C_2$ to $C_8$ alkane and alkene may be a mixture of various $C_2$ to $C_8$ alkanes and alkenes. Further details concerning the starting materials will be discussed hereinafter in connection with particular embodiments of the present invention.

Suitable diluting gases include, but are not limited to, one or more of carbon monoxide, carbon dioxide, or mixtures thereof, an inert gas, such as nitrogen, argon, helium, or mixtures thereof. A suitable molar ratio of the starting materials for the initial feed stream 22, ($C_2$ to $C_8$ alkane, $C_2$ to $C_8$ alkene, or a mixture thereof):(oxygen):(diluting gas): ($H_2O$), would be, for example, (1):(0.1 to 10):(0 to 20):(0.2 to 70), for example, including but not limited to, (1):(1 to 5.0):(0 to 10):(5 to 40).

Where it is desired to produce unsaturated carboxylic acids, it is beneficial to include steam among the starting materials. In such a case, for example, a gaseous input stream comprising a mixture of and oxygen-containing gas and a steam-containing $C_2$ to $C_8$ alkane, or a steam-containing $C_2$ to $C_8$ alkene, or a steam-containing mixture thereof, may be used. It is noted that the steam may be added to the first reaction zone separately from the $C_2$ to $C_8$ alkane, the $C_2$ to $C_8$ alkene, or the mixture thereof, and the oxygen-containing gas, as an initial feed stream and an optional steam stream, respectively.

In accordance with the process, at least a portion of the one or more oxidation products is separated from the first effluent stream, for example, by using a separator, such as the condenser, to produce an intermediate product stream and an intermediate feed stream. The intermediate product stream typically contains, but is not limited to, at least a portion of the one or more oxidation products from the first effluent stream, as well as other condensables, such as organic acids, aldehydes, ketones, and water. The intermediate product stream may be fed to additional processing apparatus (not shown) to undergo further separation and purification processes. The intermediate feed stream contains, but is not limited to, at least a portion of the unreacted oxygen, unreacted $C_2$ to $C_8$ alkane or alkene, or mixture thereof, and possibly reaction by-products such as acetic acid and carbon dioxide, and, possibly, unreacted water and unreacted ammonia, depending upon the starting materials used.

The cumulative yield of the desired oxidation product produced by the above-described process is greater than the cumulative yield of the desired oxidation product that is produced by a process that does not include both separating at least a portion of the one or more oxidation products from the first effluent stream, as well as feeding additional oxygen-containing gas to the second reaction zone. In addition, the cumulative yield of the one or more oxidation products produced by the above-described process is greater than the cumulative yield of the one or more oxidation products that is produced by a process that includes only feeding additional oxygen-containing gas to the second reaction zone, without separating at least a portion of the one or more oxidation products from the first effluent stream. The process allows for the use of starting materials containing a higher concentration of the $C_2$ to $C_8$ alkane, the $C_2$ to $C_8$ alkene, or mixture thereof. It is also believed that a greater portion of the oxygen in each subsequent reaction remains available for reacting and converting the $C_2$ to $C_8$ alkanes and alkenes.

The purity of the starting material alkene is not limited, and an alkene containing a lower alkene such as ethene, air or carbon dioxide, as impurities, may be used without any particular problem. Further, the starting material alkene may be a mixture of various alkenes. Similarly, the purity of the starting material mixture of alkene and alkane is not particularly limited, and a mixture of alkene and alkane containing a lower alkene such as ethene, a lower alkane such as methane or ethane, air or carbon dioxide, as impurities, may be used without any particular problem. Further, the starting material mixture of alkene and alkane may be a mixture of various alkenes and alkanes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the oxidation reaction of this embodiment of the present invention is not clearly understood. When it is desired to incorporate molecular oxygen in the starting materials, the oxygen-containing gas may be pure oxygen gas. However, since high purity is not required, it is usually economical to use air as the oxygen-containing gas.

The following illustrative examples are provided to further demonstrate the utility of the present invention and are not in any way construed to be limiting. Moreover, the examples provided are representative examples that broadly enable the claimed scope of the invention. In the following Examples, "propane conversion" is synonymous with "feed conversion" and was calculated in accordance with the formulas provided earlier hereinabove. Furthermore, "AA yield" means acrylic acid yield and is synonymous with "product yield" and was calculated in accordance with the formulas provided earlier hereinabove.

Unless otherwise specified, all percentages recited in the following Examples are by volume, based on the total volume of the feed or product gas stream.

EXAMPLES

Comparative Examples 1-4

MMO Catalysts

A catalyst of nominal composition $Mo_{1.0}V_{0.3}Te_{0.23}Nb_{0.17}Pd_{0.01}O_x$ was prepared in the presence of nitric acid in the following manner: 200 mL of an aqueous solution containing ammonium heptamolybdate tetrahydrate (1.0M Mo), ammonium metavanadate (0.3M V) and telluric acid (0.23M Te) formed by dissolving the corresponding salts in water at 70° C., was added to a 2000 mL rotavap flask. Then 200 mL of an aqueous solution of ammonium niobium oxalate (0.17M Nb), palladium nitrate hydrate (0.0M Pd), oxalic acid (0.155M) and nitric acid (0.24M) were added thereto. After removing the water via a rotary evaporator with a warm water bath at 50° C. and 28 mm Hg, the solid materials were further dried in a vacuum oven at 25° C. overnight and then calcined. (Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours.) The catalyst, thus obtained, was ground with a high-speed micro-mill (MS 100 from Retsch), pressed and sieved to 14-20 mesh granules for reactor evaluation. 4 g of these granules were packed into a stainless steel reactor (inside diameter: 1.1 cm) for the gas phase oxidation of propane. The reactor was heated with an electric furnace and fed with a mixture of propane, air and steam having a feed composition of 7% propane, 71% Air and 22% steam. The effluent of the reactor was condensed to a separate a liquid phase and a gas phase. The gas phase was analyzed by gas chromatography to determine the propane conversion. The liquid phase was also analyzed by gas chromatography for the yield of acrylic acid. The results along with residence time and reactor temperature are shown in Table 1 and FIGS. 1 and 2.

TABLE 1

| Examples | Residence Time (sec) | Temperature (° C.) | Propane Conversion (%) | Acrylic Acid Selectivity (%) | Acrylic Acid Yield (%) |
|---|---|---|---|---|---|
| C. Ex. 1 | 3 | 357 | 52 | 78 | 41 |
| C. Ex. 2 | 3 | 361 | 60 | 76 | 46 |
| C. Ex. 3 | 3 | 369 | 67 | 72 | 48 |
| C. Ex. 4 | 3 | 377 | 72 | 71 | 51 |

Examples 1-4

Modification of MMO Catalysts Using Pyridine

A catalyst of nominal composition $Mo_{1.0}V_{0.3}Te_{0.23}Nb_{0.17}Pd_{0.01}O_x$ was prepared in the presence of nitric acid and treated with aqueous pyridine solution in the following manner: 200 mL of an aqueous solution containing ammonium heptamolybdate tetrahydrate (1.0M Mo), ammonium metavanadate (0.3M V) and telluric acid (0.23M Te) formed by dissolving the corresponding salts in water at 70° C., was added to a 2000 mL rotavap flask. Then 200 mL of an aqueous solution of ammonium niobium oxalate (0.17M Nb), palladium nitrate hydrate (0.0M Pd), oxalic acid (0.155M) and nitric acid (0.24M) were added thereto. After removing the water via a rotary evaporator with a warm water bath at 50° C. and 28 mm Hg, the solid materials were further dried in a vacuum oven at 25° C. overnight and then calcined. (Calcination was effected by placing the solid materials in an air atmosphere and heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours.) The solid materials were ground with a high-speed micro-mill (MS 100 from Retsch), then heated in 5% pyridine in water at 80° C. for 5 hours. The solids were collected by gravity filtration, dried in vacuum oven overnight, and heated in argon atmosphere at 600° C. for 2 hours. The catalyst, thus obtained, was pressed and sieved to 14-20 mesh granules for reactor evaluation. 4 g of these granules were packed into a stainless steel reactor (inside diameter: 1.1 cm) for the gas phase oxidation of propane. The reactor was heated with an electric furnace and fed with a mixture of propane, air and steam having a feed composition of 7% propane, 71% Air and 22% steam. The effluent of the reactor was condensed to a separate a liquid phase and a gas phase. The gas phase was analyzed by gas chromatography to determine the propane conversion. The liquid phase was also analyzed by gas chromatography for the yield of acrylic acid. The results along with residence time and reactor temperature are shown in Table 2 and FIG. 1.

TABLE 2

| Examples | Residence Time (sec) | Temperature (° C.) | Propane Conversion (%) | Acrylic Acid Selectivity (%) | Acrylic Acid Yield (%) |
|---|---|---|---|---|---|
| Ex. 1 | 3 | 346 | 58 | 77 | 44 |
| Ex. 2 | 3 | 354 | 64 | 76 | 49 |
| Ex. 3 | 3 | 360 | 70 | 74 | 52 |
| Ex. 4 | 3 | 373 | 79 | 71 | 56 |

Examples 5-8

Modification of MMO Catalysts Using OA-MeOH

A catalyst of nominal composition $Mo_{1.0}V_{0.3}Te_{0.23}Nb_{0.17}Pd_{0.01}O_x$ was prepared in the presence of nitric acid and treated with 1.5% 1xalic acid in methanol in the following manner: 200 mL of an aqueous solution containing ammonium heptamolybdate tetrahydrate (1.0M Mo), ammonium metavanadate (0.3M V) and telluric acid (0.23M Te) formed by dissolving the corresponding salts in water at 70° C., was added to a 2000 mL rotavap flask. Then 200 mL of an aqueous solution of ammonium niobium oxalate (0.17M Nb), palladium nitrate hydrate (0.01M Pd), oxalic acid (0.155M) and nitric acid (0.24M) were added thereto. After removing the water via a rotary evaporator with a warm water bath at 50° C. and 28 mm Hg, the solid materials were further dried in a vacuum oven at 25° C. overnight and then calcined. (Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours.) The solid materials were ground with a high-speed micro-mill (MS 100 from Retsch), then refluxed with 1.5% oxalic acid in methanol for 5 hours. The extracted solids were collected by gravity filtration and dried in vacuum oven overnight. The catalyst, thus obtained, was pressed and sieved to 14-20 mesh granules for reactor evaluation. 4 g of these granules were packed into a stainless steel reactor (inside diameter: 1.1 cm) for the gas phase oxidation of propane. The reactor was heated with an electric furnace and fed with a mixture of propane, air and steam having a feed composition of 7% propane, 71% Air and 22% steam. The effluent of the reactor was condensed to a separate a liquid phase and a gas phase. The gas phase was analyzed by gas chromatography to determine the propane conversion. The liquid phase was also analyzed by gas chromatography for the yield of acrylic acid. The results along with residence time and reactor temperature are shown in Table 3 and FIG. 1.

TABLE 3

| Examples | Residence Time (sec) | Temperature (° C.) | Propane Conversion (%) | Acrylic Acid Selectivity (%) | Acrylic Acid Yield (%) |
|---|---|---|---|---|---|
| Ex. 5 | 3 | 343 | 54 | 81 | 44 |
| Ex. 6 | 3 | 354 | 61 | 80 | 49 |
| Ex. 7 | 3 | 366 | 70 | 78 | 54 |
| Ex. 8 | 3 | 373 | 74 | 76 | 56 |

Examples 9-12

Modification of MMO Catalysts Using Cryo-grinding

A catalyst of nominal composition $Mo_{1.0}V_{0.3}Te_{0.23}Nb_{0.17}Pd_{0.01}O_x$ was prepared in the presence of nitric acid in the following manner: 200 mL of an aqueous solution containing ammonium heptamolybdate tetrahydrate (10M Mo), ammonium metavanadate (0.3M V) and telluric acid (0.23M Te) formed by dissolving the corresponding salts in water at 70° C., was added to a 2000 mL rotavap flask. Then 200 mL of an aqueous solution of ammonium niobium oxalate (0.17M Nb), palladium nitrate hydrate (0.01M Pd), oxalic acid (0.155M) and nitric acid (0.24M) were added thereto. After removing the water via a rotary evaporator with a warm water bath at 50° C. and 28 mm Hg, the solid materials were further dried in a vacuum oven at 25° C. overnight and then calcined. (Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours.) The catalyst, thus obtained, was ground with a Freezer/Mill (Model 6750 from Spex CertiPrep™), pressed and sieved to 14-20 mesh granules for reactor evaluation. 4 g of these granules were packed into a stainless steel reactor (inside diameter: 1.1 cm) for the gas phase oxidation of propane. The reactor was heated with an electric furnace and fed with a mixture of propane, air and steam having a feed composition of 7% propane, 71% Air and 22% steam. The effluent of the reactor was condensed to a separate a liquid phase and a gas phase. The gas phase was analyzed by gas chromatography to determine the propane conversion. The liquid phase was also analyzed by gas chromatography for the yield of acrylic acid. The results along with residence time and reactor temperature are shown in Table 4 and FIG. 2.

TABLE 4

| Examples | Residence Time (sec) | Temperature (° C.) | Propane Conversion (%) | Acrylic Acid Selectivity (%) | Acrylic Acid Yield (%) |
|---|---|---|---|---|---|
| Ex. 9 | 3 | 345 | 51 | 78 | 40 |
| Ex. 10 | 3 | 355 | 58 | 77 | 45 |
| Ex. 11 | 3 | 368 | 68 | 74 | 51 |
| Ex. 12 | 3 | 380 | 75 | 73 | 55 |

Examples 13-16

Modification of MMO Catalysts Using Cryo-grinding and Soxhlet Extraction Using an Organic Solvent A catalyst of nominal composition $Mo_{1.0}V_{0.3}Te_{0.23}Nb_{0.17}Pd_{0.01}O_x$ was prepared in the presence of nitric acid and treated with methanol in the following manner: 200 mL of an aqueous solution containing ammonium heptamolybdate tetrahydrate (1.0M Mo), ammonium metavanadate (0.3M V) and telluric acid (0.23M Te) formed by dissolving the corresponding salts in water at 70° C., was added to a 2000 mL rotavap flask. Then 200 mL of an aqueous solution of ammonium niobium oxalate (0.17M Nb), palladium nitrate hydrate (0.0M Pd), oxalic acid (0.155M) and nitric acid (0.24M) were added thereto. After removing the water via a rotary evaporator with a warm water bath at 50° C. and 28 mm Hg, the solid materials were further dried in a vacuum oven at 25° C. overnight and then calcined. (Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours.) The catalyst, thus obtained, was ground with a Freezer/Mill (Model 6750 from Spex CertiPrep™), then extracted with methanol in a Soxhlet apparatus for 5 hours, and the solids were dried in vacuum oven, pressed and sieved to 14-20 mesh granules for reactor evaluation. 4 g of these granules were packed into a stainless steel reactor (inside diameter: 1.1 cm) for the gas phase oxidation of propane. The reactor was heated with an electric furnace and fed with a mixture of propane, air and steam having a feed composition of 7% propane, 71% Air and 22% steam. The effluent of the reactor was condensed to a separate a liquid phase and a gas phase. The gas phase was analyzed by gas chromatography to determine the propane conversion. The liquid phase was also analyzed by gas chromatography for the yield of acrylic acid. The results along with residence time and reactor temperature are shown in Table 5 and FIG. 2.

TABLE 5

| Examples | Residence Time (sec) | Temperature (° C.) | Propane Conversion (%) | Acrylic Acid Selectivity (%) | Acrylic Acid Yield (%) |
|---|---|---|---|---|---|
| Ex. 9 | 3 | 349 | 68 | 75 | 51 |
| Ex. 10 | 3 | 355 | 72 | 74 | 53 |

TABLE 5-continued

| Examples | Residence Time (sec) | Temperature (° C.) | Propane Conversion (%) | Acrylic Acid Selectivity (%) | Acrylic Acid Yield (%) |
|---|---|---|---|---|---|
| Ex. 11 | 3 | 361 | 76 | 72 | 55 |
| Ex. 12 | 3 | 365 | 78 | 71 | 56 |

Examples 13-16

Modification of MMO Catalysts Using Cryo-grinding and Extraction Using OA-MeOH

A catalyst of nominal composition $Mo_{1.0}V_{0.3}Te_{0.23}Nb_{0.17}Pd_{0.01}O_x$ was prepared in the presence of nitric acid and treated with 1.5% oxalic acid in methanol in the following manner: 200 mL of an aqueous solution containing ammonium heptamolybdate tetrahydrate (1.0M Mo), ammonium metavanadate (0.3M V) and telluric acid (0.23M Te) formed by dissolving the corresponding salts in water at 70° C., was added to a 2000 mL rotavap flask. Then 200 mL of an aqueous solution of ammonium niobium oxalate (0.17M Nb), palladium nitrate hydrate (0.01M Pd), oxalic acid (0.155M) and nitric acid (0.24M) were added thereto. After removing the water via a rotary evaporator with a warm water bath at 50° C. and 28 mm Hg, the solid materials were further dried in a vacuum oven at 25° C. overnight and then calcined. (Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours.) The solid materials were ground with a Freezer/Mill (Model 6750 from Spex CertiPrep), then refluxed with 1.5% oxalic acid in methanol for 5 hours. The solids were collected by gravity filtration and dried in vacuum oven over night. The catalyst, thus obtained, was pressed and sieved to 14-20 mesh granules for reactor evaluation. 4 g of these granules were packed into a stainless steel reactor (inside diameter: 1.1 cm) for the gas phase oxidation of propane. The reactor was heated with an electric furnace and fed with a mixture of propane, air and steam having a feed composition of 7% propane, 71% Air and 22% steam. The effluent of the reactor was condensed to a separate a liquid phase and a gas phase. The gas phase was analyzed by gas chromatography to determine the propane conversion. The liquid phase was also analyzed by gas chromatography for the yield of acrylic acid. The results along with residence time and reactor temperature are shown in Table 6 and FIG. 2.

TABLE 6

| Examples | Residence Time (sec) | Temperature (° C.) | Propane Conversion (%) | Acrylic Acid Selectivity (%) | Acrylic Acid Yield (%) |
|---|---|---|---|---|---|
| Ex. 9 | 3 | 338 | 62 | 81 | 50 |
| Ex. 10 | 3 | 345 | 68 | 80 | 54 |
| Ex. 11 | 3 | 353 | 73 | 78 | 57 |
| Ex. 12 | 3 | 362 | 79 | 76 | 60 |

Comparative Process Example 1

No separation of the oxidation product from the effluent stream of the first reaction zone was performed. Rather, the entire effluent stream from the first reaction zone was fed into the second reaction zone with additional oxygen, in the form of molecular oxygen. A second effluent stream exited the second reaction zone and contained, among other things, acrylic acid (AA) and unreacted propane. The compositions of the effluent streams of the first and second reaction zones were analyzed and the results of the compositional analysis and calculations for the effluent streams are presented in Table 8 below, in terms of feed conversion and AA yield attributable to each reaction zone.

TABLE 8

| Reaction Zone (Stage) | Salt Bath Temperature (° C.) | Reactor Peak Temperature (° C.) | Cumulative Propane Conversion (%) | Cumulative Acrylic Acid Yield (%) |
|---|---|---|---|---|
| First | 351 | 379 | 51.7 | 38.7 |
| Second | 352 | 364 | 80.1 | 50.6 |

Process Example 2

A portion of the oxidation product (AA) was separated from the effluent stream of the first reaction zone using the inter-condenser operating with chilled water at a temperature of 4° C. More particularly, the inter-condenser removed greater than 95 vol % of the AA formed in the first stage from the first stage effluent stream to form an intermediate product stream containing primarily AA, as well as various other by-products, including, but not limited to, water and acetic acid.

The remaining portion of the effluent stream formed an intermediate feed stream which was fed into the second reaction zone with additional oxygen, in the form of molecular oxygen, in an amount such that the feed stream to the second reaction zone was non-flammable. A second effluent stream exited the second reaction zone and contained, among other things, acrylic acid (AA) and unreacted propane. The compositions of the effluent streams of the first and second reaction zones were analyzed and the results of the compositional analysis and calculations for the intermediate product stream and the effluent streams are presented in Table 9 below in terms of feed conversion and AA yield attributable to each reaction zone.

TABLE 9

| Reaction Zone (Stage) | Salt Bath Temperature (° C.) | Reactor Peak Temperature (° C.) | Cumulative Propane Conversion (%) | Cumulative Acrylic Acid Yield (%) |
|---|---|---|---|---|
| First | 351 | 379 | 51.7 | 38.7 |
| Second | 361 | 371 | 85.3 | 60.7 |

Process Example 3

The reaction system used for this Example was identical to the reaction system used for the previous Examples, with the addition of a third reaction zone (stage) in series after the second reaction zone and a second inter-condenser positioned between the second and third reaction zones. The third reactor also contains 55 cc of MMO catalyst. Similar to the first inter-condenser, the second inter-condenser was capable of cooling the effluent stream of the second reaction zone for the purpose of separating at least a portion of the oxidation product (acrylic acid) from the effluent stream of the second reaction zone prior to being fed to the third reaction zone.

A portion of the oxidation product (AA) was separated from the effluent stream of the first reaction zone using the first inter-condenser operating with chilled water at a temperature of 4° C. More particularly, the first inter-condenser removed greater than 95 vol % of the AA formed in the first stage from the first stage effluent stream to form an intermediate product stream containing primarily AA, as well as various other by-products, including, but not limited to, water and acetic acid.

The remaining portion of the effluent stream formed an intermediate feed stream which was fed into the second reaction zone with additional oxygen, in the form of molecular oxygen. A second effluent stream exited the second reaction zone and contained, among other things, acrylic acid (AA) and unreacted propane.

A portion of the oxidation product (AA) was separated from the second effluent stream using the second inter-condenser operating with chilled water at a temperature of 4° C. More particularly, the second inter-condenser removed greater than 95 vol % of the AA formed in the second stage from the second stage effluent stream to form a second intermediate product stream containing primarily AA, as well as various other by-products, including, but not limited to, water and acetic acid.

The remaining portion of the second effluent stream formed a second intermediate feed stream which was fed into the third reaction zone with additional oxygen, in the form of molecular oxygen. A third effluent stream exited the third reaction zone and contained, among other things, acrylic acid (AA) and unreacted propane.

The compositions of both intermediate product streams and the effluent streams of the first, second and third reaction zones were analyzed. The results of the compositional analysis and calculations for the effluent streams are presented in Table 10 below in terms of feed conversion and AA yield attributable to each reaction zone.

TABLE 10

| Reaction Zone (Stage) | Salt Bath Temperature (° C.) | Reactor Peak Temperature (° C.) | Cumulative Propane Conversion (%) | Cumulative Acrylic Acid Yield (%) |
|---|---|---|---|---|
| First | 351 | 379 | 51.7 | 38.7 |
| Second | 361 | 371 | 85.3 | 60.7 |
| Third | 346 | 357 | 95.9 | 69.3 |

Post Treatment Examples of Catalysts of Different Densities

Example 13

Comparative

A catalyst of nominal composition $Mo_{1.0}V_{0.3}Te_{0.23}Nb_{0.17}Pd_{0.01}O_x$ was prepared in the presence of nitric acid and treated with methanol in the following manner: 200 mL of an aqueous solution containing ammonium heptamolybdate tetrahydrate (1.0M Mo), ammonium metavanadate (0.3M V) and telluric acid (0.23M Te) formed by dissolving the corresponding salts in water at 70° C., was added to a 2000 mL rotavap flask. Then 200 mL of an aqueous solution of ammonium niobium oxalate (0.17M Nb), palladium nitrate hydrate (0.01M Pd), oxalic acid (0.155M) and nitric acid (0.24M) were added thereto. After removing the water via a rotary evaporator with a warm water bath at 50° C. and 28 mm Hg, the solid materials were further dried in a vacuum oven at 25° C. overnight and then calcined. (Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours.) The catalyst, thus obtained, was ground with a Freezer/Mill (Model 6750 from Spex CertiPrep™), then extracted with methanol in a Soxhlet apparatus for 5 hours, and the solids were dried in vacuum oven, pressed and sieved to 14-20 mesh granules for reactor evaluation. 4 g of these granules were packed into a stainless steel reactor (inside diameter: 1.1 cm) for the gas phase oxidation of propane. The reactor was heated with an electric furnace and fed with a mixture of propane, air and steam having a feed composition of 7% propane, 71% Air and 22% steam. The effluent of the reactor was condensed to a separate a liquid phase and a gas phase. The gas phase was analyzed by gas chromatography to determine the propane conversion. The liquid phase was also analyzed by gas chromatography for the yield of acrylic acid. The results at the three second residence time and reactor temperature are shown in Table 4.

Example 14

A catalyst of nominal composition $Mo_{1.0}V_{0.3}Te_{0.23}Nb_{0.17}Pd_{0.01}O_x$ was prepared in the presence of nitric acid and treated with methanol in the following manner: 200 mL of an aqueous solution containing ammonium heptamolybdate tetrahydrate (1.0M Mo), ammonium metavanadate (0.3M V) and telluric acid (0.23M Te) formed by dissolving the corresponding salts in water at 70° C., was added to a 2000 mL rotavap flask. Then 200 mL of an aqueous solution of ammonium niobium oxalate (0.17M Nb), palladium nitrate hydrate (0.01M Pd), oxalic acid (0.155M) and nitric acid (0.24M) were added thereto. After removing the water via a rotary evaporator with a warm water bath at 50° C. and 28 mm Hg, the solid materials were further dried in a vacuum oven at 25° C. overnight and then calcined. (Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours.) The catalyst, thus obtained, was ground with a Freezer/Mill (Model 6750 from Spex CertiPrep™), then extracted with methanol in a soxhlet apparatus for 5 hours, and the solids were dried in vacuum oven, extra pressed and sieved to 14-20 mesh granules for reactor evaluation. In the extra press procedure, the o-ring sample holder for the catalyst powder was filled with an excess of 20 wt % of the catalyst powder. All other parameters during the pressing procedure were equivalent to those of example 13. 4 g of these granules were packed into a stainless steel reactor (inside diameter: 1.1 cm) for the gas phase oxidation of propane. The reactor was heated with an electric furnace and fed with a mixture of propane, air and steam having a feed composition of 7% propane, 71% Air and 22% steam. The effluent of the reactor was condensed to a separate a liquid phase and a gas phase. The gas phase was analyzed by gas chromatography to determine the propane conversion. The liquid phase was also analyzed by gas chromatography for the yield of acrylic acid. The results at the three second residence time and reactor temperature are shown in Table 11.

TABLE 11

| Example | Density | Temp ° C. | % C3 Conv. | % AA Yield |
|---------|---------|-----------|------------|------------|
| 13 | 1.38 | 373 | 72.6 | 53.0 |
| 14 | 1.65 | 371 | 77.0 | 57.6 |

From the foregoing Examples, it can be seen that the process of the present invention, including the steps of separating at least a portion of the oxidation product from effluent streams and adding additional oxygen to the reaining portion prior feeding it to subsequent reaction zones, results in higher feed conversion and higher product yield.

It will be understood that the embodiments of the present invention described hereinabove are merely exemplary and that a person skilled in the art may make variations and modifications without departing from the spirit and scope of the invention. All such variations and modifications are intended to be included within the scope of the present invention.

What is claimed:

1. A modified catalyst comprising: one or more prepared metal oxide catalysts which are altered subsequent to calcination using one or more treatments, selected from the group consisting of:
   a) chemical treatment comprising contacting with a reducing agent comprising pyridine;
   b) chemical treatment comprising extraction with oxalic acid in methanol;
   c) combined physical and chemical treatment comprising cryo-grinding followed by Soxhlet extraction with an organic solvent comprising an alcohol;
   d) combined physical and chemical treatment comprising cryo-grinding followed by extraction with oxalic acid in methanol; and
   e) chemical treatment comprising extraction with an alcohol followed by physical treatment comprising densification of the catalyst by performing an extra press procedure;

wherein the modified catalyst comprises one or more modified mixed metal oxide catalysts having the empirical formula:

$$M_eMoV_aNb_bX_cZ_dO_n$$

wherein $M_e$ is at least one chemical modifying agent selected from the group consisting of a reducing agent, an oxidizing agent, and an alcohol, X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, Y, rare earth elements and alkaline earth elements, $0.1 \leq a \leq 1.0$, $0.01 \leq b \leq 1.0$, $0.01 \leq c \leq 1.0$, $0 \leq d \leq 1.0$ and n, e are determined by the oxidation states of the other elements, and wherein the modified catalyst exhibits one or more differences in chemical, physical, structural properties and combinations thereof, as compared to the unmodified prepared catalyst.

2. The modified catalyst according to claim 1, wherein a gas phase mixture of an alkane selected from ethane, propane, butane and isobutane or an alkene selected from ethylene, propylene, butane and isobutylene or a combination of an alkane and corresponding alkene and air is converted to corresponding $C_2$, $C_3$ and $C_4$ products selected from alkenes, saturated carboxylic acids, unsaturated carboxylic acids, including acrylic acid and methacrylic, and combinations thereof upon contacting the mixture with the one or more modified catalysts.

3. A process for improving the performance of a prepared mixed metal oxide catalyst, comprising the steps of:
   a) providing precursors for a mixed metal oxide having the empirical formula:

$$M_eMoV_aNb_bX_cZ_dO_n$$

wherein $M_e$ is at least one chemical modifying agent selected from the group consisting of a reducing agent, an oxidizing agent, and an alcohol, X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, Bi, Y, rare earth elements and alkaline earth elements, $0.1 \leq a \leq 1.0$, $0.01 \leq b \leq 1.0$, $0.01 \leq c \leq 1.0$, $0 \leq d \leq 1.0$ and n, e are determined by the oxidation states of the other elements; and
   b) calcining said precursors to form said prepared mixed metal oxide catalyst; and
   c) after said calcining, altering said prepared mixed metal oxide catalyst using one or more treatments selected from the group consisting of:
      1) chemical treatment comprising contacting with a reducing agent comprising pyridine;
      2) chemical treatment comprising extraction with oxalic acid in methanol;
      3) combined physical and chemical treatment comprising cryo-grinding followed by Soxhlet extraction with an organic solvent comprising an alcohol;
      4) combined physical and chemical treatment comprising cryo-grinding followed by extraction with oxalic acid in methanol; and
      5) chemical treatment comprising extraction with an alcohol followed by physical treatment comprising densification of the catalyst by performing an extra press procedure.

* * * * *